United States Patent [19]

Soma et al.

[11] 4,166,813

[45] Sep. 4, 1979

[54] POLYALKYLATED 4-AMINOPIPERIDINE DERIVATIVES

[75] Inventors: Nobuo Soma; Syoji Morimura; Takao Yoshioka; Tomoyuki Kurumada, all of Hiromachi, Japan

[73] Assignee: Sankyo Company Ltd., Tokyo, Japan

[21] Appl. No.: 903,592

[22] Filed: May 8, 1978

[30] Foreign Application Priority Data

May 18, 1977 [JP] Japan .................................. 52/57271

[51] Int. Cl.$^2$ .................. C07D 401/12; C07D 401/14; C08K 5/34
[52] U.S. Cl. ...................... 260/45.8 N; 260/45.8 NT; 260/45.85 B; 544/222; 546/205; 546/207; 546/223; 546/224; 546/244
[58] Field of Search .................... 260/45.8 NP, 293.63, 260/293.64; 544/222

[56] References Cited

U.S. PATENT DOCUMENTS

| | | |
|---|---|---|
| 3,480,635 | 11/1969 | Altwicker ....................... 260/293.64 |
| 3,684,765 | 8/1972 | Matsui et al. ................. 260/45.8 NP |
| 3,887,517 | 6/1975 | Murayama et al. ........... 260/45.7 PH |
| 3,904,581 | 9/1975 | Murayama et al. ........... 260/45.8 NP |
| 3,993,655 | 11/1976 | Rasberger et al. ............ 260/45.8 NP |
| 4,088,629 | 5/1978 | Uhrhan et al. .................. 260/293.63 |

*Primary Examiner*—Hosea E. Taylor
*Assistant Examiner*—R. A. White
*Attorney, Agent, or Firm*—Toren, McGeady and Stanger

[57] ABSTRACT

New polyalkylated 4-aminopiperidine derivatives contain in their molecule two or three piperidine rings, each having two alkyl substituents at both the 2- and the 6-positions, optionally having substituents at the 1- and 3-positions and having an amino substituent at the 4- position. The piperidine rings are joined together by attachment of the 4-amino substituents through, where there are two piperidine rings, a polyalkylene, polyether or polyester chain, or through, where there are three piperidine rings, an isocyanurate or glycerol system. These compounds and their acid addition salts are useful as stabilizers for synthetic polymers.

16 Claims, No Drawings

POLYALKYLATED 4-AMINOPIPERIDINE DERIVATIVES

BACKGROUND OF THE INVENTION

Although a multitude of synthetic polymers has been made and is available commercially, both for domestic and industrial use, most of the commonly used synthetic polymers are very susceptible to the effects of light (particularly ultraviolet light) and heat. Exposure to light and heat, such as may be obtained simply from normal day-to-day use, will often seriously discolour or degrade the polymer, with the result that, at best, the polymer loses its aesthetic appeal and, at worst, the polymer may become completely useless. Accordingly, it is standard practice to incorporate into the majority of synthetic polymers one or more compounds, known as "polymer stabilizers", which have the effect of stabilizing the polymer against the effects of light and heat. Some classes of polyalkylated 4-aminopiperidine derivatives are disclosed in U.S. Pat. No. 3,684,765 and No. 3,904,581 and in German Offenlegungsschrift No. 2,621,870 and such compounds have been proposed for use as stabilizers for synthetic polymers. Moreover, German Offenlegungsschrift No. 2,611,208 discloses polymers whose side chains are linked to polyalkylated 4-aminopiperidine derivatives.

However, the known polyalkylated 4-aminopiperidine derivatives have a number of defects. For example, they are volatile or tend to colour the polymer in which they are incorporated and, as a result, they are not satisfactory for commercial use.

BRIEF SUMMARY OF THE INVENTION

It is, therefore, an object of the present invention to provide a class of new polyalkylated 4-aminopiperidine derivatives which do not suffer from the disadvantages of the prior art compounds.

More specifically, it is an object of the invention to provide such compounds which stabilize synthetic polymers against photo- and thermal-degradation but which are less volatile and have less colouring activity than the known compounds.

The novel polyalkylated 4-aminopiperidine derivatives of the present invention are those compounds represented by formula (I):

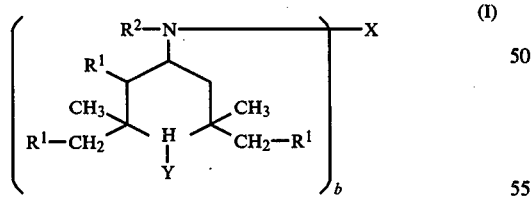

in which:
R$^1$ represents a hydrogen atom or a methyl group;
R$^2$ represents a hydrogen atom, an alkyl group having from 1 to 18 carbon atoms, a cycloalkyl group having from 5 to 7 carbon atoms, a phenyl group which is unsubstituted or has one or more C$_1$–C$_4$ alkyl and/or C$_1$–C$_4$ alkoxy substituents, a naphthyl group, an aralkyl group having 7 or 8 carbon atoms, an aliphatic, aromatic, araliphatic or alicyclic acyl group having up to 18 carbon atoms (the aryl moiety of said acyl group being unsubstituted or having one or more C$_1$–C$_4$ alkyl and/or hydroxy substituents), an alkylsulphonyl group having from 1 to 4 carbon atoms, a phenylsulphonyl group which is unsubstituted or has one or more C$_1$–C$_{12}$ alkyl substituents, a group of formula —CONHR$^3$ (in which R$^3$ represents an alkyl group having from 1 to 18 carbon atoms, a phenyl group which is unsubstituted or has one or more methyl, chlorine or bromine substituents, a naphthyl group or a cycloalkyl group having from 5 to 7 carbon atoms) or a group of formula —CH$_2$CH$_2$OZ (in which Z is as defined hereafter);

when R$^2$ represents a hydrogen atom,
Y represents a hydrogen atom, an alkyl group having from 1 to 18 carbon atoms, an alkenyl group having 3 or 4 carbon atoms or a benzyl group; and
Z represents a hydrogen atom; or when R$^2$ represents a group other than a hydrogen atom,
Y represents a hydrogen atom, an alkyl group having from 1 to 18 carbon atoms, an alkenyl group having 3 or 4 carbon atoms, a benzyl group, a 2,3-epoxypropyl group, an aliphatic acyl group having up to 18 carbon atoms or one of the groups of formula

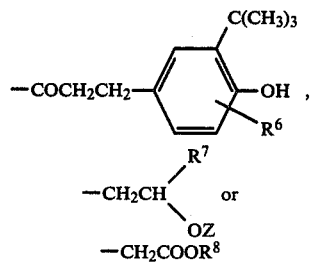

(wherein:
R$^6$ represents an alkyl group having from 1 to 4 carbon atoms;
R$^7$ represents a hydrogen atom, a methyl group or a phenyl group;
R$^8$ represents an alkyl group having from 1 to 18 carbon atoms; and
Z is as defined hereafter); and
Z represents a hydrogen atom, an alkyl group having from 1 to 18 carbon atoms, an allyl group, a benzyl group, an aliphatic, aromatic, araliphatic or alicyclic acyl group having up to 18 carbon atoms (the aryl moiety of said acyl group being unsubstituted or having one or more C$_1$–C$_4$ alkyl and/or hydroxy substituents) or a group of formula —CONHR$^9$ (in which R$^9$ represents an alkyl group having from 1 to 18 carbon atoms, a phenyl group which is unsubstituted or has one or more methyl, chlorine or bromine substituents, a naphthyl group or a cycloalkyl group having from 5 to 7 carbon atoms);
b is 2 or 3; and
when b=2
X represents one of the groups of formula

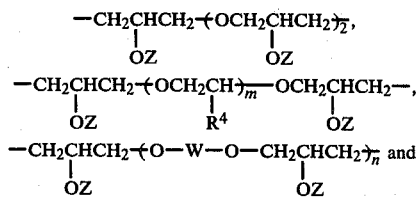

-continued

—CH₂CHCH₂—
      |
      OZ

[wherein:
m and n each represents an integer of from 1 to 10;
R⁴ represents a hydrogen atom or a methyl group;
W represents one of the groups of formula

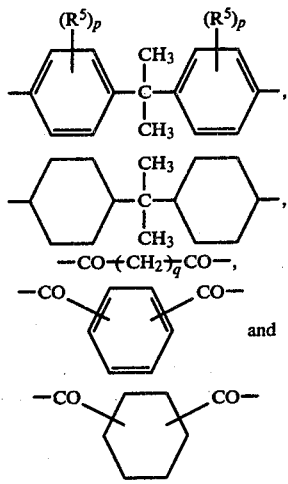

—CO—(CH₂)_q—CO—, and (wherein
p represents 0, 1 or 2;
R⁵ represents a halogen atom; and
q represents an integer of from 1 to 10); and
Z is defined above]; or
when b=3,
X represents one of the groups of formula

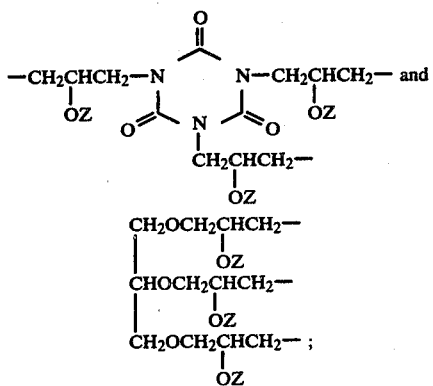

CH₂OCH₂CHCH₂—
           |
           OZ
CHOCH₂CHCH₂—
    |
    OZ
CH₂OCH₂CHCH₂— ;
           |
           OZ and acid addition salts thereof.

These polyalkylated 4-aminopiperidine derivatives and their acid addition salts are valuable stabilizers and have less volatility and impart less colour than do similar known stabilizers.

The invention therefore also provides a polymer composition comprising a synthetic polymer and one or more of the polyalkylated 4-aminopiperidine derivatives or acid addition salts of the invention, in an amount sufficient to stabilize the synthetic polymer against photo- or thermal-deterioration.

DETAILED DESCRIPTION OF INVENTION

In the compounds of formula (I), when R² represents an alkyl group having from 1 to 18 carbon atoms, it may be, for example, a methyl, ethyl, n-propyl, n-butyl, n-octyl, 2-ethylhexyl, dodecyl or octadecyl group, and is preferably an alkyl group having from 1 to 8, and most preferably from 1 to 4, carbon atoms.

When R² represents a cycloalkyl group having from 5 to 7 carbon atoms, it may be a cyclopentyl, cyclohexyl or cycloheptyl group and is preferably a cyclohexyl group.

When R² is an optionally substituted phenyl group, it may be, for example phenyl itself or an o-tolyl, m-tolyl, p-tolyl, p-ethylphenyl, p-n-butylphenyl, o-methoxyphenyl, m-methoxyphenyl, p-methoxyphenyl, p-ethoxyphenyl or p-butoxyphenyl group. It is preferably a phenyl group optionally having a methyl or methoxy substituent, and is most preferably a phenyl group.

When R² represents a naphthyl group, it may be an α- or β-naphthyl group.

When R² represents an aralkyl group having 7 or 8 carbon atoms, it may be, for example, a benzyl, phenethyl or p-methylbenzyl group, preferably a benzyl group.

When R² represents an aliphatic, aromatic, araliphatic or cycloaliphatic acyl group having up to 18 carbon atoms and whose aryl moiety optionally has one or more $C_1$–$C_4$ alkyl and/or hydroxy substituents, it is preferably a group of formula —COR¹⁰. In this group, R¹⁰ represents: an alkyl group having from 1 to 17 carbon atoms; an alkenyl group having 2 or 3 carbon atoms; a phenyl group which is unsubstituted or has from 1 to 3 $C_1$–$C_4$ alkyl and/or hydroxy substituents (which may be the same or different); a benzyl group; a 4-hydroxy-3,5-di-t-butylphenethyl group; or a cyclohexyl group. When R¹⁰ represents a substituted phenyl group, the phenyl group is preferably substituted either by one $C_1$–$C_4$ alkyl group or by two $C_1$–$C_4$ alkyl groups and one hydroxy group. Examples of such acyl groups are: acetyl, propionyl, valeryl, octanoyl, 2-ethylhexanoyl, lauroyl, palmitoyl, stearoyl, acryloyl, crotonoyl, methacryloyl, benzoyl, o-toluoyl, m-toluoyl, p-toluoyl, p-t-butylbenzoyl, salicyloyl, 4-hydroxy-3,5-di-t-butylbenzoyl, phenylacetyl, 3-(4-hydroxy-3,5-di-t-butylphenyl)propionyl or cyclohexanecarbonyl. More preferably the acyl group is an alkanoyl group having from 2 to 18 carbon atoms, a benzoyl group or a 3-(4-hydroxy-3,5-di-t-butylphenyl)propionyl group. Most preferably, the acyl group is an alkanoyl group having from 2 to 12 carbon atoms or a benzoyl group, especially an acetyl group.

When R² represents an alkylsulphonyl group having from 1 to 4 carbon atoms or a phenylsulphonyl group (which is optionally substituted by a $C_1$–$C_{12}$ alkyl group), it may be, for example, a methylsulphonyl, ethylsulphonyl, n-butylsulphonyl, benzenesulphonyl, o-toluenesulphonyl, p-toluenesulphonyl or p-dodecylbenzenesulphonyl group, preferably a benzenesulphonyl or p-toluenesulphonyl group.

When R² represents a group of formula —CONHR³, R³ may represent: an alkyl group having from 1 to 18 carbon atoms (e.g. a methyl, ethyl, n-butyl, octyl or octadecyl group); a phenyl group optionally having one or more methyl, chlorine or bromine substituents (e.g. phenyl, o-tolyl, m-tolyl, p-tolyl, o-chlorophenyl, m-chlorophenyl, p-chlorophenyl, o-bromophenyl, m-bromophenyl or p-bromophenyl); an α- or β-naphthyl group; or a cycloalkyl group having from 5 to 7 carbon atoms (e.g. a cyclopentyl or cyclohexyl group). R³ preferably represents an alkyl group having from 1 to 4 carbon atoms or a phenyl group, most preferably a phenyl group.

When b is 2 and X represents the group

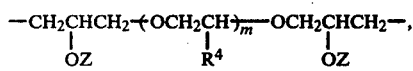

m is an integer from 1 to 10 and is preferably 1, and $R^4$ represents a hydrogen atom or a methyl group, preferably a hydrogen atom.

When X represents the group

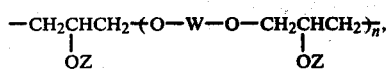

n represents a integer of from 1 to 10, preferably from 1 to 3 and most preferably 1.

When W represents a group of formula

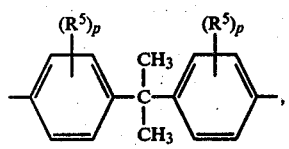

p may be 0, 1 or 2 and $R^5$ represents a halogen atom, e.g. chlorine or bromine. We prefer those compounds in which p is 0, i.e. the benzene rings in the group represented by W are unsubstituted. Examples of such groups are:

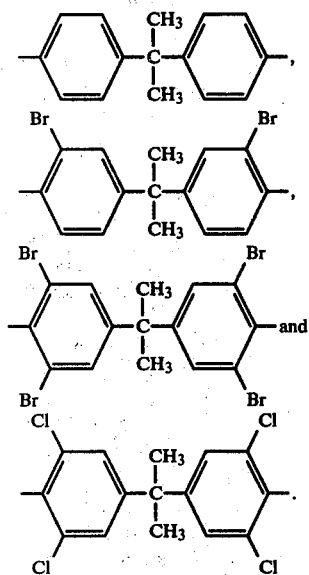

When W represents a group formula —CO—$(CH_{2q}$—CO—, q represents an integer of from 1 to 10, preferably from 2 to 8 and most preferably 4. Examples of such groups include malonyl, succinyl, adipoyl, suberoyl, sebacoyl and dodecan edioyl.

Other groups which may be represented by W are phthaloyl, isophthaloyl, terephthaloyl, 1,2-cyclohexanedicarbonyl, 1,3-cyclohexanedicarbonyl and 1,4-cyclohexanedicarbonyl, of which we particularly prefer phthaloyl and 1,2-cyclohexanedicarbonyl.

When Y represents an alkyl group having from 1 to 18 carbon atoms, it may be, for example, a methyl, ethyl, n-propyl, n-butyl, octyl, dodecyl or octadecyl group, preferably an alkyl group having from 1 to 4 carbon atoms and most preferably a methyl group.

When Y represents an alkenyl group having 3 or 4 carbon atoms, it may be, for example, an allyl or a 2-butenyl group, preferably an allyl group.

When Y represents an aliphatic acyl group having up to 18 carbon atoms, it may be an alkanoyl group (for example an acetyl, propionyl, butyryl, octanoyl, lauroyl, palmitoyl or stearoyl group) or an alkenoyl group (for example an acryloyl or crotonoyl group), preferably an alkanoyl group having from 2 to 4 carbon atoms, or an alkenoyl group having 3 or 4 carbon atoms, most preferably acetyl. Where Y represents an aliphatic acyl group and Z represents an aliphatic acyl group, the two groups are preferably identical. Similarly, where Y, $R^2$ and Z all represent aliphatic acyl groups, the groups are all preferably identical.

When Y represents a group of formula

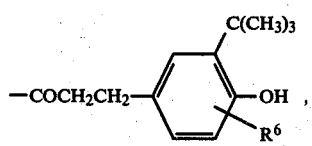

$R^6$ represents an alkyl group having from 1 to 4 carbon atoms, for example a methyl, ethyl or t-butyl group, preferably a t-butyl group. Examples of such groups represented by Y are the 3-(4-hydroxy-3-methyl-5-t-butylphenyl)propionyl and 3-(4-hydroxy-3,5-di-t-butylphenyl)propionyl groups.

When Y represents a group of formula

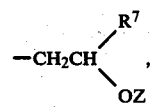

$R^7$ represents a hydrogen atom, a methyl group or a phenyl group, preferably a hydrogen atom, and Z is as defined hereafter.

When Y represents a group of formula —CH$_2$COOR$^8$, R$^8$ represents an alkyl group having from 1 to 18 carbon atoms, for example a methyl, ethyl, n-butyl, octyl, dodecyl or octadecyl group, preferably an alkyl group having from 1 to 4 carbon atoms.

When Z represents an alkyl group having from 1 to 18 carbon atoms, it may be, for example, methyl, ethyl, n-propyl, n-butyl, octyl, dodecyl or octadecyl, preferably an alkyl group having from 1 to 8 carbon atoms, more preferably a methyl or ethyl group and most preferably a methyl group.

When Z represents an aliphatic, aromatic, araliphatic or alicyclic acyl group having up to 18 carbon atoms (in which the aryl moiety optionally has one or more $C_1$-$C_4$ alkyl and/or hydroxy substituents), it is preferably a group of formula —COR$^{11}$. In this formula, R$^{11}$ represents an alkyl group having from 1 to 17 carbon atoms; an alkenyl group having 2 or 3 carbon atoms; a phenyl group which is unsubstituted or has from 1 to 3 substituents selected from $C_1$-$C_4$ alkyl and/or hydroxy groups; a benzyl group; a 4-hydroxy-3,5-di-t-butylphenethyl group; or a cyclohexyl group. Where R$^{11}$ represents a substituted phenyl group, the substituents preferably consist either of a single alkyl group or of two alkyl groups and one hydroxy group. Examples of acyl groups represented by the formula —COR$^{11}$ are the same as the examples of groups represented by the formula —COR$^{10}$. More preferably, the acyl groups is an alkanoyl group having from 2 to 18 carbon atoms, a benzoyl group or a 3-(4-hydroxy-3,5-di-t-butylphenyl)-propionyl group. Most preferably the acyl group is an alkanoyl group having from 2 to 12 carbon atoms or a benzoyl group, especially an acetyl group. We prefer that, where Z represents an acyl group, it is identical with the acyl group represented by R$^2$.

When Z represents a group of formula —CONHR$^9$, R$^9$ may be any one of the groups exemplified above in respect of R$^3$. In particular, we prefer that, when Z represents a group of formula —CONHR$^9$, it is a group identical with that of formula —CONHR$^3$ represented by R$^2$.

Of the polyalkylated 4-aminopiperidine derivatives of formula (I), we prefer the following classes of compound:

compounds wherein R$^1$ represents a hydrogen atom;
compounds wherein R$^2$ represents a hydrogen atom, an alkyl group having from 1 to 8 carbon atoms, a cyclohexyl group, an alkanoyl group having from 2 to 12 carbon atoms, a benzoyl group or a group of formula —CH$_2$CH$_2$OZ' (in which Z' represents a hydrogen atom, an acetyl group or a benzoyl group), especially a hydrogen atom, an alkyl group having from 1 to 8 carbon atoms, an acetyl group or a 2-hydroxyethyl group;
compounds wherein X represents a group of formula

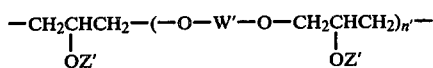

[in which W' represents one of the groups

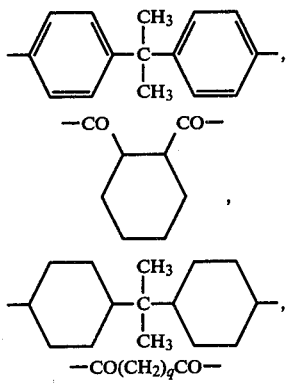

—CO(CH$_2$)$_q$CO—

(in which q is an integer from 1 to 10) or

—CH$_2$CH$_2$—, n' is 0 or 1 and Z' is as defined above; more preferably W' is

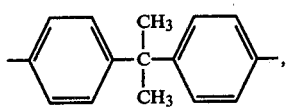

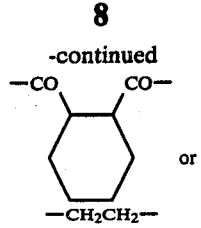

and n' is 1];
compounds in which Y represents a hydrogen atom, a methyl group, an allyl group or an acetyl group, especially a hydrogen atom or a methyl group;
compounds wherein Z represents a hydrogen atom, an acetyl group or a benzoyl group, especially a hydrogen atom; and
compounds wherein b is 2.

Preferred compounds of the present invention are represented by formula (II):

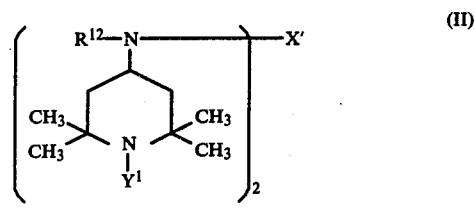

wherein:
R$^{12}$ represents a hydrogen atom, an alkyl group having from 1 to 8 carbon atoms or a 2-hydroxyethyl group;
X' represents a group of formula

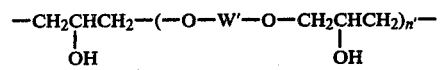

(in which W' and n' are as defined above); and
Y' represents a hydrogen atom or a methyl group.

In the case of the compounds of formula (I) in which R$^1$ represents a methyl group, the compounds can exist in the form of various stereoisomers, and the present invention embraces both the individual stereoisomers as well as mixtures of any two or more thereof.

The present invention also provides acid addition salts of the compounds of formula (I). The nature of the acid employed to form such acid addition salts is not critical, provided that, where the acid addition salt is to be used to stabilize a polymer, the acid employed does not adversely affect the stability of the polymer. Examples of suitable acids include: inorganic acids, such as sulphuric acid, hydrochloric acid and phosphoric acid; organic carboxylic acids, such as formic acid, acetic acid, valeric acid, stearic acid, oxalic acid, adipic acid, sebacic acid, maleic acid, benzoic acid, p-t-butylbenzoic acid, 4-hydroxy-3,5-di-t-butylbenzoic acid, salicyclic acid and terephthalic acid; sulphonic acids, such as methanesulphonic acid and p-toluenesulphonic acid; and organic phosphonic acids, such as phenylphosphonic acid.

The following is a non-limiting list of individual polyalkylated 4-aminopiperidine derivatives of formula (I). The numbers appended to the compounds in this list will be used to identify them hereinafter in the Examples.

Compounds of formula (I):

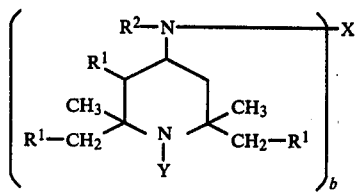

wherein:

(A) b=2 and X represents the group

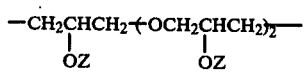

and in which $R^1$, $R^2$, Y and Z are as shown in Table A.

Table A

| Compound No. | $R^1$ | $R^2$ | Y | Z |
|---|---|---|---|---|
| 1 | H | —$C_4H_9$ | H | H |
| 2 | H | —$C_4H_9$ | —$CH_3$ | H |
| 3 | H | —$C_4H_9$ | —$CH_3$ | —$COCH_3$ |

(B) b=2, $R^1$ represents a hydrogen atom and X represents a group of formula

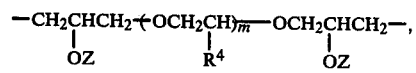

and in which $R^2$, Y, m, $R^4$ and Z are as shown in Table B;

Table B

| Compound No. | $R^2$ | Y | m | $R^4$ | Z |
|---|---|---|---|---|---|
| 4 | —$C_4H_9$ | H | 1 | H | H |
| 5 | —$C_4H_9$ | —$CH_3$ | 1 | H | H |
| 6 | —$C_4H_9$ | —$CH_3$ | 1 | H | —$CH_3$ |
| 7 | —$C_4H_9$ | —$CH_3$ | 1 | H | —$COCH_3$ |
| 8 | —$C_4H_9$ | H | 1 | H | —$COC_{11}H_{23}$ |
| 9 | —$C_4H_9$ | H | 1 | H | —CO—C$_6$H$_5$ |
| 10 | —$C_4H_9$ | H | 1 | H | —COCH$_2$CH$_2$—C$_6$H$_2$(C(CH$_3$)$_3$)$_2$OH |
| 11 | —$C_4H_9$ | H | 1 | H | —CONHCH$_3$ |
| 12 | —$C_4H_9$ | —COCH$_3$ | 1 | H | —COCH$_3$ |
| 13 | —CH$_2$CH$_2$OH | H | 1 | H | H |
| 14 | —CH$_3$ | H | 1 | —CH$_3$ | H |
| 15 | —CH$_3$ | H | 9 | H | H |

(C) b=2 and X represents the group

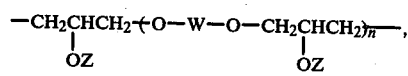

and in which $R^1$, $R^2$, Y, n, W and Z are as shown in following Table C;

TABLE C

| Compound No. | R¹ | R² | Y | n | W | Z |
|---|---|---|---|---|---|---|
| 16 | H | H | H | 1 | 4-CH₃-C₆H₄-C(CH₃)₂-C₆H₄- | H |
| 17 | H | H | —CH₃ | 1 | 4-CH₃-C₆H₄-C(CH₃)₂-C₆H₄- | H |
| 18 | H | H | —C₈H₁₇ | 1 | 4-CH₃-C₆H₄-C(CH₃)₂-C₆H₄- | H |
| 19 | H | H | —CH₂CH=CH₂ | 1 | 4-CH₃-C₆H₄-C(CH₃)₂-C₆H₄- | H |
| 20 | H | H | —CH₂—C₆H₅ | 1 | 4-CH₃-C₆H₄-C(CH₃)₂-C₆H₄- | H |
| 21 | H | —CH₃ | H | 1 | 4-CH₃-C₆H₄-C(CH₃)₂-C₆H₄- | H |
| 22 | H | —CH₃ | —CH₃ | 1 | 4-CH₃-C₆H₄-C(CH₃)₂-C₆H₄- | H |
| 23 | H | —CH₃ | —CH₂CH₂OH | 1 | 4-CH₃-C₆H₄-C(CH₃)₂-C₆H₄- | H |
| 24 | H | —CH₃ | —CH₂COOCH₃ | 1 | 4-CH₃-C₆H₄-C(CH₃)₂-C₆H₄- | H |

TABLE C-continued

| Compound No. | R¹ | R² | Y | n | W | Z |
|---|---|---|---|---|---|---|
| 25 | H | —CH₃ | —CH₂COOCH₃ | 1 | -C(CH₃)₂- diphenyl | —COC₄H₉ |
| 26 | H | —CH₃ | —CH₂COOCH₃ | 1 | -C(CH₃)₂- diphenyl | —COCH(CH₂)₃CH₃ with C₂H₅ |
| 27 | H | —CH₃ | —CH₂COOCH₃ | 1 | -C(CH₃)₂- diphenyl | —COC₁₁H₂₃ |
| 28 | H | —CH₃ | —CH₂COOCH₃ | 1 | -C(CH₃)₂- diphenyl | —COC₁₇H₃₅ |
| 29 | H | —CH₃ | —CH₂COOCH₃ | 1 | -C(CH₃)₂- diphenyl | —CO—O—C₆H₅ |
| 30 | H | —CH₃ | —CH₂COOCH₃ | 1 | -C(CH₃)₂- diphenyl | —CO-(3,5-di-t-butyl-4-hydroxyphenyl) |
| 31 | H | —CH₃ | —CH₂COOCH₃ | 1 | -C(CH₃)₂- diphenyl | —COCH₂CH₂-(3,5-di-t-butyl-4-hydroxyphenyl) |
| 32 | H | —CH₃ | —CH₂COOCH₃ | 1 | -C(CH₃)₂- diphenyl | —CONHCH₃ |

TABLE C-continued

| Compound No. | R¹ | R² | Y | n | W | Z |
|---|---|---|---|---|---|---|
| 33 | H | —CH₃ | —CH₂COOCH₃ | 1 | -C(CH₃)₂- bis(p-tolyl) | —CONH—C₆H₅ |
| 34 | H | —CH₃ | —CH₃ | 1 | -C(CH₃)₂- bis(p-tolyl) | —CH₃ |
| 35 | H | —CH₃ | —CH₃ | 1 | -C(CH₃)₂- bis(p-tolyl) | —COCH₃ |
| 36 | H | —CH₃ | —CH₃ | 1 | -C(CH₃)₂- bis(p-tolyl) | —COC(=CH₂)CH₃ |
| 37 | H | —CH₃ | —CH₃ | 1 | -C(CH₃)₂- bis(p-tolyl) | —CO—C₆H₅ |
| 38 | H | —CH₃ | —CH₃ | 1 | -C(CH₃)₂- bis(p-tolyl) | —CO—C₆H₄—CH₃ (p) |
| 39 | H | —CH₃ | —CH₃ | 1 | -C(CH₃)₂- bis(p-tolyl) | —CONHC₂H₅ |
| 40 | H | —CH₃ | —CH₃ | 1 | -C(CH₃)₂- bis(p-tolyl) | —CONH—C₆H₄—CH₃ (m) |
| 41 | H | —CH₃ | —C₂H₅ | 1 | -C(CH₃)₂- bis(p-tolyl) | —C₂H₅ |

TABLE C-continued

| Compound No. | R¹ | R² | Y | n | W | Z |
|---|---|---|---|---|---|---|
| 42 | H | —CH₃ | —C₁₂H₂₅ | 1 | -C(CH₃)₂- diphenyl | —C₁₂H₂₅ |
| 43 | H | —CH₃ | —CH₂—C₆H₅ | 1 | -C(CH₃)₂- diphenyl | —CH₂—C₆H₅ |
| 44 | H | —CH₃ | —CH₂—CH—CH₂ (epoxide) | 1 | -C(CH₃)₂- diphenyl | —C₄H₉ |
| 45 | H | —CH₃ | —COCH₃ | 1 | -C(CH₃)₂- diphenyl | —COCH₃ |
| 46 | H | —CH₃ | —COC₁₁H₂₃ | 1 | -C(CH₃)₂- diphenyl | —COC₁₁H₂₃ |
| 47 | H | —CH₃ | —COC₁₇H₃₅ | 1 | -C(CH₃)₂- diphenyl | —COC₁₇H₃₅ |
| 48 | H | —CH₃ | —COCH=CH₂ | 1 | -C(CH₃)₂- diphenyl | —COCH=CH₂ |
| 49 | H | —CH₃ | —CH₂CH₂OCH₃ | 1 | -C(CH₃)₂- diphenyl | —CH₃ |
| 50 | H | —CH₃ | —CH₂CH₂OCH₂— | 1 | -C(CH₃)₂- diphenyl | —CH₂—C₆H₅ |

TABLE C-continued

| Compound No. | R¹ | R² | Y | n | W | Z |
|---|---|---|---|---|---|---|
| 51 | H | —CH₃ | —CH₂CH₂OCOC₁₇H₃₅ | 1 | —C(CH₃)₂—(di-p-tolyl) | —COC₁₇H₃₅ |
| 52 | H | —CH₃ | —CH₂CH₂OCO—C₆H₅ | 1 | —C(CH₃)₂—(di-p-tolyl) | —O—C₆H₅ |
| 53 | H | —CH₃ | —CH₂CH₂OCO—(2-hydroxyphenyl) | 1 | —C(CH₃)₂—(di-p-tolyl) | —O—(2-hydroxyphenyl) |
| 54 | H | —CH₃ | —CH₂CH₂OCO—CH₂—(3,5-di-tert-butyl-4-hydroxyphenyl) | 1 | —C(CH₃)₂—(di-p-tolyl) | —COCH₂—(3,5-di-tert-butyl-4-hydroxyphenyl) |
| 55 | H | —CH₃ | —CH₂CHOCOCH₃ (CH₃) | 1 | —C(CH₃)₂—(diphenyl) | —COCH₃ |
| 56 | H | —CH₃ | —CH₂CHOCOCH₃ (C₆H₅) | 1 | —C(CH₃)₂—(diphenyl) | —COCH₃ |
| 57 | H | —CH₃ | —CH₂COOC₁₈H₃₇ | 1 | —C(CH₃)₂—(diphenyl) | —C₁₈H₃₇ |
| 58 | H | —C₂H₅ | H | 1 | —C(CH₃)₂—(diphenyl) | H |

TABLE C-continued
| Compound No. | R¹ | R² | Y | n | W | Z |
|---|---|---|---|---|---|---|
| 59 | H | —C₂H₅ | —CH₃ | 1 | 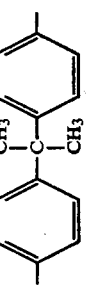 | H |
| 60 | H | —C₂H₅ | H | 1 | 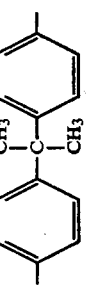 | —COC₁₁H₂₃ |
| 61 | H | —C₂H₅ | H | 1 | 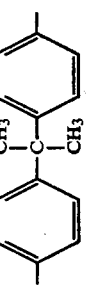 | 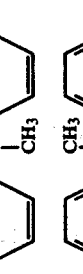 |
| 62 | H | —C₂H₅ | H | 1 | 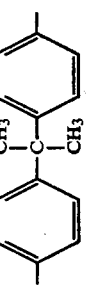 | 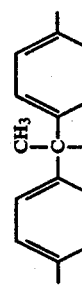 |
| 63 | H | —C₂H₅ | H | 1 | 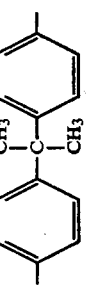 | 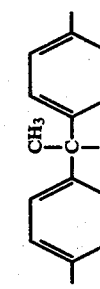 |
| 64 | H | —C₂H₅ | H | 1 | 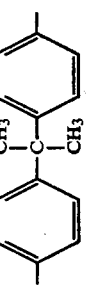 | —CONHC₈H₁₇ |
| 65 | H | —C₂H₅ | —CH₃ | 1 | 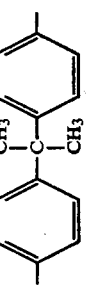 | —CH₃ |
| 66 | H | —C₂H₅ | —CH₃ | 1 | 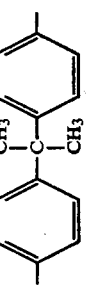 | —COCH₃ |

TABLE C-continued

| Compound No. | R¹ | R² | Y | n | W | Z |
|---|---|---|---|---|---|---|
| 67 | H | —C₂H₅ | —C₂H₅ | 1 | 4-CH₃-C₆H₄—C(CH₃)₂—C₆H₄-4- | —C₂H₅ |
| 68 | H | —C₂H₅ | —COCH₃ | 1 | 4-CH₃-C₆H₄—C(CH₃)₂—C₆H₄-4- | —COCH₃ |
| 69 | H | —C₂H₅ | —CH₂CH₂OCOC₇H₁₅ | 1 | 4-CH₃-C₆H₄—C(CH₃)₂—C₆H₄-4- | —COC₇H₁₅ |
| 70 | H | —C₄H₉ | H | 1 | 4-CH₃-C₆H₄—C(CH₃)₂—C₆H₄-4- | H |
| 71 | H | —C₄H₉ | —CH₃ | 1 | 4-CH₃-C₆H₄—C(CH₃)₂—C₆H₄-4- | H |
| 72 | H | —C₄H₉ | —C₄H₉ | 1 | 4-CH₃-C₆H₄—C(CH₃)₂—C₆H₄-4- | H |
| 73 | H | —C₄H₉ | —CH₂CH=CH₂ | 1 | 4-CH₃-C₆H₄—C(CH₃)₂—C₆H₄-4- | H |
| 74 | H | —C₄H₉ | —CH₂—C₆H₅ | 1 | 4-CH₃-C₆H₄—C(CH₃)₂—C₆H₄-4- | H |
| 75 | H | —C₄H₉ | —CH₂CH₂OH | 1 | 4-CH₃-C₆H₄—C(CH₃)₂—C₆H₄-4- | H |

TABLE C-continued

| Compound No. | R¹ | R² | Y | n | W | Z |
|---|---|---|---|---|---|---|
| 76 | H | $-C_4H_9$ | $-CH_2CHOH-C_6H_5$ | 1 | $-C_6H_4-C(CH_3)_2-C_6H_4-$ | H |
| 77 | H | $-C_4H_9$ | H | 1 | $-C_6H_4-C(CH_3)_2-C_6H_4-$ | $-COC_{11}H_{23}$ |
| 78 | H | $-C_4H_9$ | H | 1 | $-C_6H_4-C(CH_3)_2-C_6H_4-$ | $-CO-O-C_6H_5$ |
| 79 | H | $-C_4H_9$ | H | 1 | $-C_6H_4-C(CH_3)_2-C_6H_4-$ | $-CO-O-C_6H_2(C(CH_3)_3)_2OH$ |
| 80 | H | $-C_4H_9$ | H | 1 | $-C_6H_4-C(CH_3)_2-C_6H_4-$ | $-CONH-C_6H_4-CH_3$ |
| 81 | H | $-C_4H_9$ | $-CH_3$ | 1 | $-C_6H_4-C(CH_3)_2-C_6H_4-$ | $-CH_3$ |
| 82 | H | $-C_4H_9$ | $-CH_3$ | 1 | $-C_6H_4-C(CH_3)_2-C_6H_4-$ | $-COC_{11}H_{23}$ |
| 83 | H | $-C_4H_9$ | $-CH_3$ | 1 | $-C_6H_4-C(CH_3)_2-C_6H_4-$ | $-CO-O-C_6H_5$ |
| 84 | H | $-C_4H_9$ | $-CH_3$ | 1 | $-C_6H_4-C(CH_3)_2-C_6H_4-$ | $-CO-O-C_6H_4-CH_3$ |

TABLE C-continued

| Compound No. | R¹ | R² | Y | n | W | Z |
|---|---|---|---|---|---|---|
| 85 | H | —C₄H₉ | —CH₃ | 1 | 4-CH₃-C₆H₄−C(CH₃)₂−C₆H₄-4-CH₃ | —COCH₂CH₂−(3,5-di-t-Bu-4-OH-C₆H₂) |
| 86 | H | —C₄H₉ | —CH₃ | 1 | 4-CH₃-C₆H₄−C(CH₃)₂−C₆H₄-4-CH₃ | —CONHC₄H₉ |
| 87 | H | —C₄H₉ | —CH₃ | 1 | 4-CH₃-C₆H₄−C(CH₃)₂−C₆H₄-4-CH₃ | —CONH−C₆H₅ |
| 88 | H | —C₄H₉ | —CH₃ | 1 | 4-CH₃-C₆H₄−C(CH₃)₂−C₆H₄-4-CH₃ | —CONH−C₆H₄-4-Cl |
| 89 | H | —C₄H₉ | —CH₂CH=CH₂ | 1 | 4-CH₃-C₆H₄−C(CH₃)₂−C₆H₄-4-CH₃ | —CH₂CH=CH₂ |
| 90 | H | —C₄H₉ | —COCH₃ | 1 | 4-CH₃-C₆H₄−C(CH₃)₂−C₆H₄-4-CH₃ | —COCH₃ |
| 91 | H | —C₄H₉ | —COC₃H₇ | 1 | 4-CH₃-C₆H₄−C(CH₃)₂−C₆H₄-4-CH₃ | —COC₃H₇ |
| 92 | H | —C₄H₉ | —COCH₂CH₂−(3,5-di-t-Bu-4-OH-C₆H₂) | 1 | 4-CH₃-C₆H₄−C(CH₃)₂−C₆H₄-4-CH₃ | —COCH₂CH₂−(3,5-di-t-Bu-4-OH-C₆H₂) |

TABLE C-continued

| Compound No. | R¹ | R² | Y | n | W | Z |
|---|---|---|---|---|---|---|
| 93 | H | —C₄H₉ | —CH₂CH₂OCOCH₃ | 1 | bisphenol (C(CH₃)₂ bridge, p-CH₃) | —COCH₃ |
| 94 | H | —C₄H₉ | —CH₂CH₂OCO—C₆H₅ | 1 | bisphenol | —CO—C₆H₅ |
| 95 | H | —C₄H₉ | —CH₂CH₂OCONHCH₃ | 1 | bisphenol | —CONHCH₃ |
| 96 | H | —C₄H₉ | —CH₂CH₂OCO—CH₂CH₂—(3,5-di-t-butyl-4-hydroxyphenyl) | 1 | bisphenol | —COCH₂CH₂—(3,5-di-t-butyl-4-hydroxyphenyl) |
| 97 | H | —C₄H₉ | —CH₂COOC₈H₁₇ | 1 | bisphenol | —C₈H₁₇ |
| 98 | H | —C₄H₁₇ | H | 1 | bisphenol | H |
| 99 | H | —C₈H₁₇ | —CH₃ | 1 | bisphenol | H |
| 100 | H | —C₈H₁₇ | —C₈H₃₇ | 1 | bisphenol | H |
| 101 | H | —C₈H₁₇ | —CH₂CH₂OH | 1 | bisphenol | H |

TABLE C-continued

| Compound No. | $R^1$ | $R^2$ | Y | n | W | Z |
|---|---|---|---|---|---|---|
| 102 | H | $-C_8H_{17}$ | $-CH_2CHOH$<br>$\quad\quad\;\;CH_3$ | 1 | 4-methylphenyl-C(CH_3)_2-phenyl- | H |
| 103 | H | $-C_8H_{17}$ | H | 1 | 4-methylphenyl-C(CH_3)_2-phenyl- | $-COC_{11}H_{23}$ |
| 104 | H | $-C_8H_{17}$ | H | 1 | 4-methylphenyl-C(CH_3)_2-phenyl- | $-CO-$phenyl |
| 105 | H | $-C_8H_{17}$ | H | 1 | 4-methylphenyl-C(CH_3)_2-phenyl- | $-CO-$(3,5-di-t-butyl-4-hydroxyphenyl) |
| 106 | H | $-C_8H_{17}$ | H | 1 | 4-methylphenyl-C(CH_3)_2-phenyl- | $-COCH_2CH_2-$(3,5-di-t-butyl-4-hydroxyphenyl) |
| 107 | H | $-C_8H_{17}$ | H | 1 | 4-methylphenyl-C(CH_3)_2-phenyl- | $-CONHCH_3$ |
| 108 | H | $-C_8H_{17}$ | $-CH_3$ | 1 | 4-methylphenyl-C(CH_3)_2-phenyl- | $-CH_3$ |
| 109 | H | $-C_8H_{17}$ | $-CH_3$ | 1 | 4-methylphenyl-C(CH_3)_2-phenyl- | $-CH_2-$phenyl |

TABLE C-continued

| Compound No. | R¹ | R² | Y | n | W | Z |
|---|---|---|---|---|---|---|
| 110 | H | —C₈H₁₇ | —CH₃ | 1 | —C₆H₄—C(CH₃)₂—C₆H₄— | —O—C₆H₄—CH₃ (m) |
| 111 | H | —C₈H₁₇ | —COCH₃ | 1 | —C₆H₄—C(CH₃)₂—C₆H₄— | —COCH₃ |
| 112 | H | —C₈H₁₇ | —CH₃ | 1 | —C₆H₄—C(CH₃)₂—C₆H₄— | —COC₁₁H₂₃ |
| 113 | H | —CH₂CH(CH₂)₃CH₃ <br> \|  <br> C₂H₅ | H | 1 | —C₆H₄—C(CH₃)₂—C₆H₄— | H |
| 114 | H | —CH₂CH(CH₂)₃CH₃ <br> \|  <br> C₂H₅ | —CH₃ | 1 | —C₆H₄—C(CH₃)₂—C₆H₄— | H |
| 115 | H | —CH₂CH(CH₂)₃CH₃ <br> \|  <br> C₂H₅ | —CH₂CH=CHCH₃ | 1 | —C₆H₄—C(CH₃)₂—C₆H₄— | H |
| 116 | H | —CH₂CH(CH₂)₃CH₃ <br> \|  <br> C₂H₅ | H | 1 | —C₆H₄—C(CH₃)₂—C₆H₄— | —COC₁₁H₂₃ |
| 117 | H | —CH₂CH(CH₂)₃CH₃ <br> \|  <br> C₂H₅ | H | 1 | —C₆H₄—C(CH₃)₂—C₆H₄— | —O—C₆H₅ |
| 118 | H | —CH₂CH(CH₂)₃CH₃ <br> \|  <br> C₂H₅ | —CH₃ | 1 | —C₆H₄—C(CH₃)₂—C₆H₄— | —CH₃ |

TABLE C-continued
| Compound No. | $R^1$ | $R^2$ | Y | n | W | Z |
|---|---|---|---|---|---|---|
| 119 | H | —CH$_2$CH(CH$_2$)$_3$CH$_3$<br>       C$_2$H$_5$ | —COCH$_3$ | 1 | 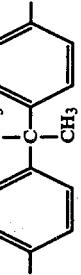 | —COCH$_3$ |
| 120 | H | —CH$_2$CH(CH$_2$)$_3$CH$_3$<br>       C$_2$H$_5$ | —COCH=CHCH$_3$ | 1 | 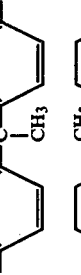 | —COCH=CHCH$_3$ |
| 121 | H | —C$_{18}$H$_{37}$ | H | 1 | 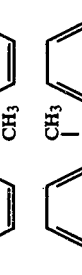 | H |
| 122 | H | —C$_{18}$H$_{37}$ | —CH$_3$ | 1 | 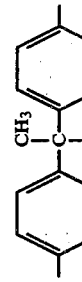 | H |
| 123 | H | —C$_{18}$H$_{37}$ | H | 1 | 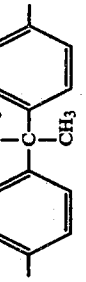 | —COC$_{11}$H$_{23}$ |
| 124 | H | —C$_{18}$H$_{37}$ | H | 1 | 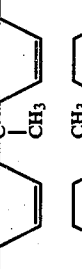 | 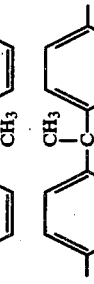 |
| 125 | H | —C$_{18}$H$_{37}$ | —COCH$_3$ | 1 | 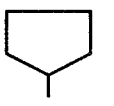 | —COCH$_3$ |
| 126 | H | 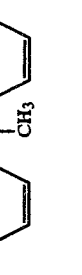 | H | 1 |  | H |
| 127 | H |  | H | 1 | | H |

TABLE C-continued

| Compound No. | R¹ | R² | Y | n | W | Z |
|---|---|---|---|---|---|---|
| 128 | H | cyclohexyl | —CH₃ | 1 | —C(C₆H₄)(CH₃)₂—C₆H₄— | H |
| 129 | H | cyclohexyl | H | 1 | —C(C₆H₄)(CH₃)₂—C₆H₄— | —COC₁₁H₂₃ |
| 130 | H | cyclohexyl | H | 1 | —C(C₆H₄)(CH₃)₂—C₆H₄— | —OC₆H₅ |
| 131 | H | cyclohexyl | H | 1 | —C(C₆H₄)(CH₃)₂—C₆H₄— | —COCH₂CH₂-(3,5-di-tert-butyl-4-hydroxyphenyl) |
| 132 | H | cycloheptyl | —CH₃ | 1 | —C(C₆H₄)(CH₃)₂—C₆H₄— | —CH₃ |
| 133 | H | cycloheptyl | —COCH₃ | 1 | —C(C₆H₄)(CH₃)₂—C₆H₄— | —COCH₃ |
| 134 | H | cycloheptyl | H | 1 | —C(C₆H₄)(CH₃)₂—C₆H₄— | H |
| 135 | H | cycloheptyl | —CH₃ | 1 | —C(C₆H₄)(CH₃)₂—C₆H₄— | H |
| 136 | H | cyclohexenyl | H | 1 | —C(C₆H₄)(CH₃)₂—C₆H₄— | H |

TABLE C-continued

| Compound No. | R¹ | R² | Y | n | W | | Z |
|---|---|---|---|---|---|---|---|
| 137 | H | phenyl | —CH₃ | 1 | 4-methylphenyl | C(CH₃)₂-(4-methylphenyl) | H |
| 138 | H | phenyl | —COCH₃ | 1 | 4-methylphenyl | C(CH₃)₂-(4-methylphenyl) | —COCH₃ |
| 139 | H | 3-methylphenyl | H | 1 | 4-methylphenyl | C(CH₃)₂-(4-methylphenyl) | H |
| 140 | H | 4-C₄H₉-phenyl | H | 1 | 4-methylphenyl | C(CH₃)₂-(4-methylphenyl) | H |
| 141 | H | 4-OCH₃-phenyl | H | 1 | 4-methylphenyl | C(CH₃)₂-(4-methylphenyl) | H |
| 142 | H | 4-OC₄H₉-phenyl | H | 1 | 4-methylphenyl | C(CH₃)₂-(4-methylphenyl) | H |
| 143 | H | 1-naphthyl | H | 1 | 4-methylphenyl | C(CH₃)₂-(4-methylphenyl) | H |
| 144 | H | —CH₂-phenyl | H | 1 | 4-methylphenyl | C(CH₃)₂-(4-methylphenyl) | H |
| 145 | H | —CH₂CH₂-phenyl | H | 1 | 4-methylphenyl | C(CH₃)₂-(4-methylphenyl) | H |

TABLE C-continued

| Compound No. | R¹ | R² | Y | n | W | Z |
|---|---|---|---|---|---|---|
| 146 | H | $-COCH_3$ | H | 1 | (structure) | H |
| 147 | H | $-COCH_3$ | $-CH_3$ | 1 | (structure) | H |
| 148 | H | $-COCH_3$ | $-CH_2C_6H_5$ | 1 | (structure) | H |
| 149 | H | $-COCH_3$ | $-CH_3$ | 1 | (structure) | $-COCH_3$ |
| 150 | H | $-COCH_3$ | $-COCH_3$ | 1 | (structure) | $-COCH_3$ |
| 151 | H | $-COC_{11}H_{23}$ | H | 1 | (structure) | $-COC_{11}H_{23}$ |
| 152 | H | $-COC_{17}H_{35}$ | H | 1 | (structure) | $-COC_{17}H_{35}$ |
| 153 | H | $-COCH=CH_2$ | $-CH_3$ | 1 | (structure) | $-COCH=CH_2$ |
| 154 | H | $-COCH=CHCH_3$ | $-CH_3$ | 1 | (structure) | $-COCH=CHCH_3$ |

Where W is:

$$p\text{-}CH_3\text{-}C_6H_4\text{-}C(CH_3)_2\text{-}C_6H_4\text{-}$$

(4-methylphenyl group connected via $-C(CH_3)_2-$ to a phenyl ring)

TABLE C-continued

| Compound No. | R¹ | R² | Y | n | W | Z |
|---|---|---|---|---|---|---|
| 155 | H | -COCH₂-[3,5-di-t-butyl-4-hydroxyphenyl] | H | 1 | -C₆H₄-C(CH₃)₂-C₆H₄- | -COCH₂CH₂-[3,5-di-t-butyl-4-hydroxyphenyl] |
| 156 | H | -CO-C₆H₅ | H | 1 | -C₆H₄-C(CH₃)₂-C₆H₄- | -CO-C₆H₅ |
| 157 | H | -CO-[3,5-di-t-butyl-4-hydroxyphenyl] | H | 1 | -C₆H₄-C(CH₃)₂-C₆H₄- | -CO-[3,5-di-t-butyl-4-hydroxyphenyl] |
| 158 | H | -COCH₂-C₆H₅ | H | 1 | -C₆H₄-C(CH₃)₂-C₆H₄- | -COCH₂-C₆H₅ |
| 159 | H | -CO-C₆H₁₁ | H | 1 | -C₆H₄-C(CH₃)₂-C₆H₄- | -CO-C₆H₁₁ |
| 160 | H | -SO₂CH₃ | H | 1 | -C₆H₄-C(CH₃)₂-C₆H₄- | H |
| 161 | H | -SO₂C₄H₉ | -CH₃ | 1 | -C₆H₄-C(CH₃)₂-C₆H₄- | H |
| 162 | H | -SO₂-C₆H₅ | H | 1 | -C₆H₄-C(CH₃)₂-C₆H₄- | H |

TABLE C-continued

| Compound No. | R¹ | R² | Y | n | W | Z |
|---|---|---|---|---|---|---|
| 163 | H | ―SO₂―C₆H₄―CH₃ (p-tolyl) | H | 1 | ―C₆H₄―C(CH₃)₂―C₆H₄― | H |
| 164 | H | ―SO₂―C₆H₄―C₁₂H₂₅ | H | 1 | ―C₆H₄―C(CH₃)₂―C₆H₄― | H |
| 165 | H | ―CONHCH₃ | H | 1 | ―C₆H₄―C(CH₃)₂―C₆H₄― | ―CONHCH₃ |
| 166 | H | ―CONHC₄H₉ | H | 1 | ―C₆H₄―C(CH₃)₂―C₆H₄― | ―CONHC₄H₉ |
| 167 | H | ―CONHC₁₈H₃₇ | H | 1 | ―C₆H₄―C(CH₃)₂―C₆H₄― | ―CONHC₁₈H₃₇ |
| 168 | H | ―CONH―C₆H₅ | H | 1 | ―C₆H₄―C(CH₃)₂―C₆H₄― | H |
| 169 | H | ―CONH―C₆H₄―CH₃ | H | 1 | ―C₆H₄―C(CH₃)₂―C₆H₄― | H |
| 170 | H | ―CONH―(1-naphthyl) | H | 1 | ―C₆H₄―C(CH₃)₂―C₆H₄― | H |
| 171 | H | ―CONH―cyclohexyl | H | 1 | ―C₆H₄―C(CH₃)₂―C₆H₄― | H |

TABLE C-continued

| Compound No. | $R^1$ | $R^2$ | Y | n | W | Z |
|---|---|---|---|---|---|---|
| 172 | H | —CH$_2$CH$_2$OH | H | 1 | 4-CH$_3$-C$_6$H$_4$-C(CH$_3$)$_2$-C$_6$H$_4$- | H |
| 173 | H | —CH$_2$CH$_2$OCH$_3$ | —CH$_3$ | 1 | 4-CH$_3$-C$_6$H$_4$-C(CH$_3$)$_2$-C$_6$H$_4$- | —CH$_3$ |
| 174 | H | —CH$_2$CH$_2$OC$_8$H$_{17}$ | —CH$_2$CH$_2$OC$_8$H$_{17}$ | 1 | 4-CH$_3$-C$_6$H$_4$-C(CH$_3$)$_2$-C$_6$H$_4$- | —C$_8$H$_{17}$ |
| 175 | H | —CH$_2$CH$_2$OC$_{18}$H$_{37}$ | —CH$_2$CH$_2$OC$_{18}$H$_{37}$ | 1 | 4-CH$_3$-C$_6$H$_4$-C(CH$_3$)$_2$-C$_6$H$_4$- | —C$_{18}$H$_{37}$ |
| 176 | H | —CH$_2$CH$_2$OCH$_2$CH=CH$_2$ | —CH$_2$CH$_2$OCH$_2$CH=CH$_2$ | 1 | 4-CH$_3$-C$_6$H$_4$-C(CH$_3$)$_2$-C$_6$H$_4$- | —CH$_2$CH=CH$_2$ |
| 177 | H | —CH$_2$CH$_2$OCH$_2$-C$_6$H$_5$ | H | 1 | 4-CH$_3$-C$_6$H$_4$-C(CH$_3$)$_2$-C$_6$H$_4$- | —CH$_2$-C$_6$H$_5$ |
| 178 | H | —CH$_2$CH$_2$OCOCH$_3$ | —COCH$_3$ | 1 | 4-CH$_3$-C$_6$H$_4$-C(CH$_3$)$_2$-C$_6$H$_4$- | —COCH$_3$ |
| 179 | H | —CH$_2$CH$_2$OCOC$_{11}$H$_{23}$ | H | 1 | 4-CH$_3$-C$_6$H$_4$-C(CH$_3$)$_2$-C$_6$H$_4$- | —COC$_{11}$H$_{23}$ |
| 180 | H | —CH$_2$CH$_2$OCOC$_{17}$H$_{35}$ | —CH$_3$ | 1 | 4-CH$_3$-C$_6$H$_4$-C(CH$_3$)$_2$-C$_6$H$_4$- | —COC$_{17}$H$_{35}$ |

TABLE C-continued

| Compound No. | R¹ | R² | Y | n | W | Z |
|---|---|---|---|---|---|---|
| 181 | H | —CH₂CH₂OCO—(phenyl) | H | 1 | 4,4′-isopropylidenediphenyl | —O—(phenyl) |
| 182 | H | —CH₂CH₂OCO—(3,5-di-tert-butyl-4-hydroxyphenyl) | —CH₂CH₂OCO—(3,5-di-tert-butyl-4-hydroxyphenyl) | 1 | 4,4′-isopropylidenediphenyl | —O—(3,5-di-tert-butyl-4-hydroxyphenyl) |
| 183 | H | —CH₂CH₂OCOCH₂—(phenyl) | —CH₂CH₂OCOCH₂—(phenyl) | 1 | 4,4′-isopropylidenediphenyl | —OCOCH₂—(phenyl) |
| 184 | H | —CH₂CH₂OCO—CH₂CH₂—(3,5-di-tert-butyl-4-hydroxyphenyl) | H | 1 | 4,4′-isopropylidenediphenyl | —OCOCH₂CH₂—(3,5-di-tert-butyl-4-hydroxyphenyl) |
| 185 | H | —CH₂CH₂OCO—(cyclohexyl) | —CH₂CH₂OCO—(cyclohexyl) | 1 | 4,4′-isopropylidenediphenyl | —O—(cyclohexyl) |
| 186 | H | —CH₂CH₂OCOC(=CH₂)CH₃ | —CH₂CH₂OCOC(=CH₂)CH₃ | 1 | 4,4′-isopropylidenediphenyl | —OCOC(=CH₂)CH₃ |
| 187 | H | —CH₂CH₂OCONHCH₃ | H | 1 | 4,4′-isopropylidenediphenyl | —CONHCH₃ |
| 188 | H | —CH₂CH₂OCONHC₄H₉ | —CH₂CH₂OCONHC₄H₉ | 1 | 4,4′-isopropylidenediphenyl | —CONHC₄H₉ |

TABLE C-continued

| Compound No. | R¹ | R² | Y | n | W | Z |
|---|---|---|---|---|---|---|
| 189 | H | —CH$_2$CH$_2$OCONHC$_{18}$H$_{37}$ | H | 1 | C(CH$_3$)$_2$ diphenyl | —CONHC$_{18}$H$_{37}$ |
| 190 | H | —CH$_2$CH$_2$OCONH-(phenyl) | —CH$_3$ | 1 | C(CH$_3$)$_2$ diphenyl | —CONH-(phenyl) |
| 191 | H | —CH$_2$CH$_2$OCONH-(4-CH$_3$-phenyl) | —CH$_2$CH$_2$OCONH-(4-CH$_3$-phenyl) | 1 | C(CH$_3$)$_2$ diphenyl | —CONH-(4-CH$_3$-phenyl) |
| 192 | H | —CH$_2$CH$_2$OCONH-(4-Cl-phenyl) | H | 1 | C(CH$_3$)$_2$ diphenyl | —CONH-(4-Cl-phenyl) |
| 193 | H | —CH$_2$CH$_2$OCONH-(naphthyl) | —CH$_3$ | 1 | C(CH$_3$)$_2$ diphenyl | —CONH-(naphthyl) |
| 194 | H | —CH$_2$CH$_2$OCONH-(cyclohexyl) | —CH$_2$CH$_2$OCONH-(cyclohexyl) | 1 | C(CH$_3$)$_2$ diphenyl | —CONH-(cyclohexyl) |
| 195 | H | —CH$_3$ | H | 3 | C(CH$_3$)$_2$ diphenyl | H |
| 196 | H | —C$_4$H$_9$ | H | 3 | C(CH$_3$)$_2$ diphenyl | H |
| 197 | —CH$_3$ | —CH$_3$ | H | 1 | C(CH$_3$)$_2$ diphenyl | H |

TABLE C-continued

| Compound No. | R¹ | R² | Y | n | W | Z |
|---|---|---|---|---|---|---|
| 198 | —CH₃ | —C₄H₉ | —CH₃ | 1 | bis(4-methylphenyl)(dimethyl)methyl | —COCH₃ |
| 199 | —CH₃ | —C₄H₉ | H | 1 | bis(4-methylphenyl)(dimethyl)methyl | —CO—C₆H₅ |
| 200 | —CH₃ | —COCH₃ | H | 1 | bis(4-methylphenyl)(dimethyl)methyl | —COCH₃ |
| 201 | —CH₃ | —CH₂CH₂OH | H | 1 | bis(4-methylphenyl)(dimethyl)methyl | H |
| 202 | H | —C₄H₉ | H | 1 | bis(3,5-dibromo-4-methylphenyl)(dimethyl)methyl | H |
| 203 | H | —C₄H₉ | H | 1 | bis(3,5-dichloro-4-methylphenyl)(dimethyl)methyl | H |
| 204 | H | H | H | 1 | bis(4-methylcyclohexyl)(dimethyl)methyl | H |
| 205 | H | —CH₃ | H | 1 | bis(4-methylcyclohexyl)(dimethyl)methyl | H |

TABLE C-continued

| Compound No. | R¹ | R² | Y | n | W | Z |
|---|---|---|---|---|---|---|
| 206 | H | —CH₃ | —CH₃ | 1 | —C₆H₁₀—C(CH₃)₂—C₆H₁₀— | H |
| 207 | H | —CH₃ | —COCH₃ | 1 | —C₆H₁₀—C(CH₃)₂—C₆H₁₀— | —COCH₃ |
| 208 | H | —CH₃ | H | 1 | —C₆H₁₀—C(CH₃)₂—C₆H₁₀— | —OC₆H₅ |
| 209 | H | —CH₂CH₂OH | H | 1 | —C₆H₁₀—C(CH₃)₂—C₆H₁₀— | H |
| 210 | H | H | H | 1 | —CO(CH₂)₄CO— | H |
| 211 | H | H | CH₃ | 1 | —CO(CH₂)₄CO— | H |
| 212 | H | —CH₃ | H | 1 | —CO(CH₂)₄CO— | H |
| 213 | H | —C₄H₉ | H | 1 | —CO(CH₂)₄CO— | H |
| 214 | H | —C₄H₉ | —CH₃ | 1 | —CO(CH₂)₄CO— | H |
| 215 | H | —C₄H₉ | —COCH₃ | 1 | —CO(CH₂)₄CO— | —COCH₃ |
| 216 | H | —C₈H₁₇ | —CH₃ | 1 | —CO(CH₂)₄CO— | H |
| 217 | H | —CH₂CH₂OH | —CH₃ | 1 | —CO(CH₂)₄CO— | H |
| 218 | H | —C₄H₉ | H | 1 | —CO(CH₂)₈CO— | H |
| 219 | H | —C₄H₉ | H | 1 | —CO(CH₂)₁₀CO— | H |
| 220 | H | —C₄H₉ | H | 1 | —CO—C₆H₄—CO— (ortho) | H |
| 221 | H | —C₄H₉ | —CH₃ | 1 | —CO—C₆H₄—CO— (ortho) | H |
| 222 | H | —C₄H₉ | H | 1 | —CO—C₆H₄—CO— (ortho) | —COC₁₁H₂₃ |

TABLE C-continued

| Compound No. | R¹ | R² | Y | n | W | Z |
|---|---|---|---|---|---|---|
| 223 | H | —C₄H₉ | —COCH₃ | 1 | 1,2-benzenedicarbonyl | —COCH₃ |
| 224 | H | —C₄H₉ | H | 1 | 1,3-benzenedicarbonyl | H |
| 225 | H | —C₄H₉ | H | 1 | 1,4-benzenedicarbonyl | H |
| 226 | H | H | —CH₃ | 1 | 1,2-cyclohexanedicarbonyl | H |
| 227 | H | —C₄H₉ | H | 1 | 1,2-cyclohexanedicarbonyl | H |
| 228 | H | —C₄H₉ | —CH₃ | 1 | 1,2-cyclohexanedicarbonyl | H |
| 229 | H | —C₄H₉ | H | 1 | 1,2-cyclohexanedicarbonyl | —COC₁₁H₂₃ |
| 230 | H | —C₄H₉ | H | 1 | 1,2-cyclohexanedicarbonyl | —OC₆H₅ |

TABLE C-continued

| Compound No. | R¹ | R² | Y | n | W | Z |
|---|---|---|---|---|---|---|
| 231 | H | —C₄H₉ | H | 1 | 1,2-cyclohexane-di(CO—) | —CONHCH₃ |
| 232 | H | —C₄H₉ | H | 1 | 1,2-cyclohexane-di(CO—) | —CONH-C₆H₅ |
| 233 | H | —C₄H₉ | —CH₃ | 1 | 1,2-cyclohexane-di(CO—) | —CH₃ |
| 234 | H | —CH₂CH₂OH | —CH₃ | 1 | 1,2-cyclohexane-di(CO—) | H |
| 235 | H | —C₄H₉ | H | 1 | 1,3-cyclohexane-di(CO—) | H |
| 236 | H | —C₄H₉ | H | 1 | 1,4-cyclohexane-di(CO—) | H |

(D) b=2 and X represents the group $$-CH_2CHCH_2-,$$
$$\phantom{-CH_2C}|$$
$$\phantom{-CH_2CH}OZ$$

and in which $R^1$, $R^2$, Y and Z are as shown in Table D;

Table D

| Compound No. | $R^1$ | $R^2$ | Y | Z |
|---|---|---|---|---|
| 237 | H | H | H | H |
| 238 | H | H | —$CH_3$ | H |
| 239 | H | —$CH_3$ | H | H |
| 240 | H | —$CH_3$ | —$CH_3$ | H |
| 241 | H | —$CH_3$ | H | —$COCH_3$ |
| 242 | H | —$CH_3$ | H | —$COC_{11}H_{23}$ |
| 243 | H | —$CH_3$ | H | —CO—C$_6$H$_5$ |
| 244 | H | —$CH_3$ | —$CH_3$ | —$CH_3$ |
| 245 | H | —$CH_3$ | —$CH_3$ | —$CONHCH_3$ |
| 246 | H | —$C_4H_9$ | H | H |
| 247 | H | —$C_4H_9$ | —$CH_3$ | H |
| 248 | H | —$C_4H_9$ | —$CH_2CH_2OH$ | H |
| 249 | H | —$C_4H_9$ | H | —$COC_{11}H_{23}$ |
| 250 | H | —$C_4H_9$ | H | —CONH—C$_6$H$_5$ |
| 251 | H | —$C_4H_9$ | —$COCH_3$ | —$COCH_3$ |
| 252 | H | —$C_8H_{17}$ | H | H |
| 253 | H | —$C_8H_{17}$ | H | —$COC_7H_{15}$ |
| 254 | H | —$C_{18}H_{37}$ | H | H |
| 255 | H | —$COCH_3$ | —$COCH_3$ | —$COCH_3$ |
| 256 | H | —$COC_{11}H_{23}$ | H | —$COC_{11}H_{23}$ |
| 257 | H | —CO—C$_6$H$_5$ | H | —CO—C$_6$H$_5$ |
| 258 | H | —$CONHC_2H_5$ | H | —$CONHC_2H_5$ |
| 259 | —$CH_3$ | —$C_4H_9$ | H | H |
| 260 | —$CH_3$ | —$C_4H_9$ | —$COCH_3$ | —$COCH_3$ |

(E) b=3 and X represents the group

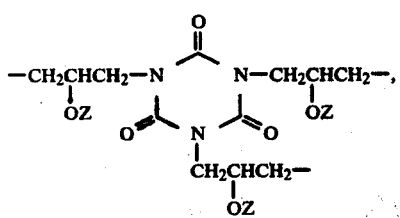

and in which $R^1$, $R^2$, Y and Z are as shown in Table E;

Table E

| Compound No. | $R^1$ | $R^2$ | Y | Z |
|---|---|---|---|---|
| 261 | H | —$CH_3$ | H | H |
| 262 | H | —$CH_3$ | —$CH_3$ | H |

(F) b=3 and X represents the group $$CH_2OCH_2CHCH_2-$$
$$\phantom{CH_2OCH_2C}|$$
$$\phantom{CH_2OCH_2CH}OZ$$
$$CHOCH_2CHCH_2-,$$
$$\phantom{CHOCH_2C}|$$
$$\phantom{CHOCH_2CH}OZ$$
$$CH_2OCH_2CHCH_2-$$
$$\phantom{CH_2OCH_2C}|$$
$$\phantom{CH_2OCH_2CH}OZ$$

and in which $R^1$, $R^2$, Y and Z are as shown in Table F;

Table F

| Compound No. | $R^1$ | $R^2$ | Y | Z |
|---|---|---|---|---|
| 263 | H | —$CH_3$ | H | H |
| 264 | H | —$CH_3$ | —$CH_3$ | H |

The polyalkylated 4-aminopiperidine derivatives of formula (I) and their acid addition salts may be prepared by any one of the following methods, which can be performed under per se known conditions.

METHOD 1

Compounds of formula (I) in which $R^2$ and Y both represent hydrogen atoms and X represents a group of formula

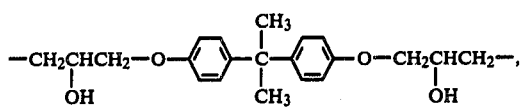

that is to say compounds of formula (III), may be prepared by reacting a compound of formula (IV) with an epoxy compound of formula (V), according to the following reaction scheme:

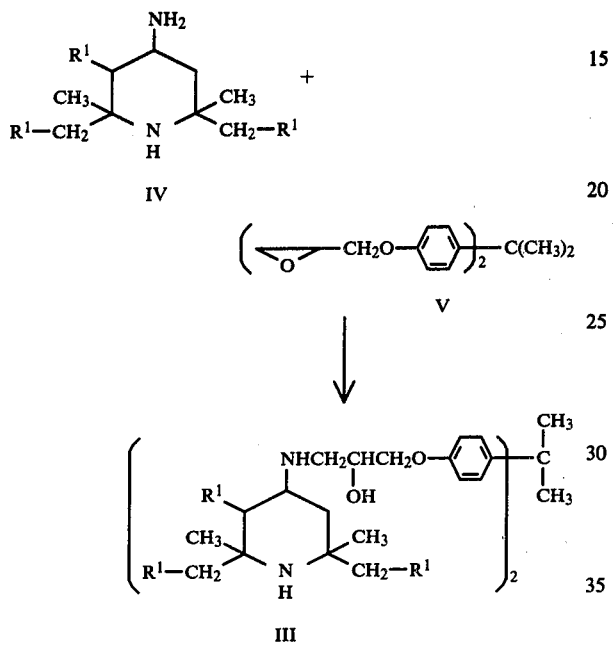

The method may also be applied to compounds of formula (I) in which $R^2$ and Y are hydrogen atoms and in which X represents one of the groups

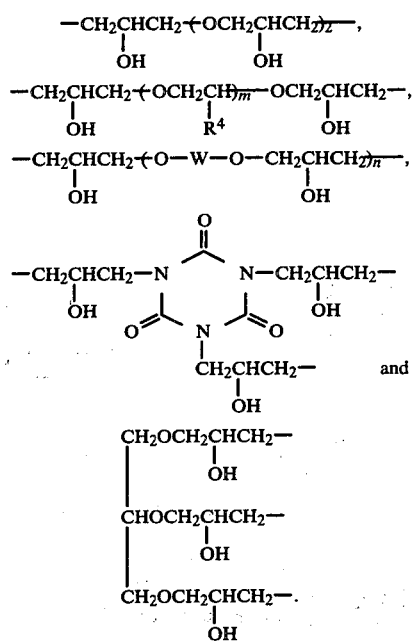

Preparation of the compound of formula (IV) used as starting material is described in, for example, German Offenlegungsschrift No. 2,621,870.

The reaction is preferably carried out by heating the compound of formula (IV) with the epoxy compound corresponding to the group X which it is desired to introduce, preferably at a temperature of from 50° to 180° C. The compound of formula (IV) is preferably employed in an amount slightly in excess of the stoichiometric amount. The reaction may be carried out in the presence or absence of an inert organic solvent and, where a solvent is employed, its nature is not critical, provided that it has no adverse effect upon the reaction. Examples of suitable solvents include: ethers, such as dioxane and diethylene glycol dimethyl ether; N,N-dialkylamides, such as N,N-di-methylformamide and N,N-dimethylacetamide; aromatic hydrocarbons, such as benzene, toluene and xylene; chlorinated aromatic hydrocarbons, such as chlorobenzene and p-dichlorobenzene; alcohols, such as methanol, ethanol, n-butanol, t-butanol and n-octanol; and aqueous alcohols, particularly aqueous methanol and aqueous ethanol. Of these solvents, alcohols and aqueous alcohols are preferred.

METHOD 2

It is also possible to prepare compounds of formula (I) in which $R^2$ and Y represent hydrogen atoms and X represents a group of formula —$CH_2CH(OH)CH_2$— by reacting a compound of formula (IV) with a halogen compound of formula (VII), according to the following reaction scheme:

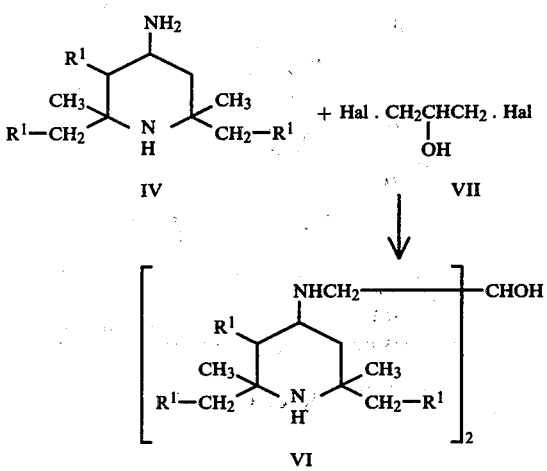

(in which $R^1$ is as defined above and Hal represents a halogen, preferably chlorine or bromine, atom).

The reaction is preferably carried out in an inert organic solvent by reacting the compound (IV) with the halogen compound (VII) in the presence of an acid-binding agent. Examples of preferred acid-binding agents are alkali metal hydroxides (such as sodium hydroxide or potassium hydroxide) and alkali metal carbonates (such as potassium carbonate). Examples of suitable solvents include: ethers, such as dioxane, tetrahydrofuran and diethyl ether; aromatic hydrocarbons, such as benzene, toluene and xylene; alcohols, such as methanol, ethanol and n-propanol; amides, such as N,N-dimethylformamide, N,N-di-methylacetamide and hexamethylphosphoric triamide; and mixtures thereof with water.

The reaction is preferably carried out at a temperature which may vary from ambient temperature to about 150° C.

The above reaction schemes involve the preparation of compounds of formula (I) in which $R^2$, Y and Z all represent hyrogen atoms. The following Methods illustrate the preparation of compounds in which $R^2$ and/or Y and/or Z represent groups other than hydrogen atoms.

METHOD 3

Compounds of formula (I) in which Y and Z both represent hydrogen atoms and $R^2$ represents an alkyl group, a cycloalkyl group, an optionally substituted phenyl group, a naphthyl group, an arylkyl group or a 2-hydroxyethyl group may be prepared by either of Methods 1 and 2, but using a compound corresponding to the compound of formula (IV) but whose 4-amino group is substituted by the desired group $R^2$.

In particular, compounds of formula (X), i.e. compounds in which Y represents a hydrogen atom, $R^2$ represents one of the above groups and X represents a group of formula —$CH_2CH(OH)CH_2$— may be prepared by reacting a compound of formula (VIII) with a compound of formula (IX), according to the following reaction scheme:

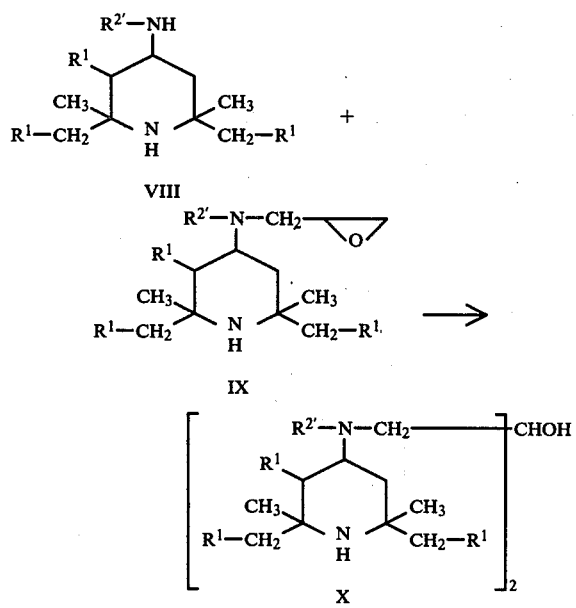

(in which $R^1$ is as defined above and $R^{2'}$ represents an alkyl group, a cycloalkyl group, an optionally substituted phenyl group, a naphthyl group, an aralkyl group or a 2-hydroxyethyl group).

The reaction is preferably carried out by reacing the compound of formula (VIII) with the compound of formula (IX) at a temperature which may range from ambient temperature to about 100° C. in the presence or absence, preferably in the presence, of an inert organic solvent. There is no particular limitation upon the nature of the solvent, provided that it has no adverse effect upon the reaction. Examples of suitable solvents include: ethers, such as dioxane and diethylene glycol dimethyl ether; N,N-dialkylamides, such as N,N-dimethylformamide and N,N-dimethylacetamide; aromatic hydrocarbons, such as benzene, toluene and xylene; chlorinated aromatic hydrocarbons, such as chlorobenzene and p-dichlorobenzene; alcohols, such as methanol, ethanol, n-butanol, t-butanol and n-octanol; and aqueous alcohols, especially aqueous methanol and aqueous ethanol.

METHOD 4

As a further alternative, compounds of formula (X), defined above, may be prepared by reacting a compound of formula (XI) with a compound of formula (XII), according to the following reaction scheme;

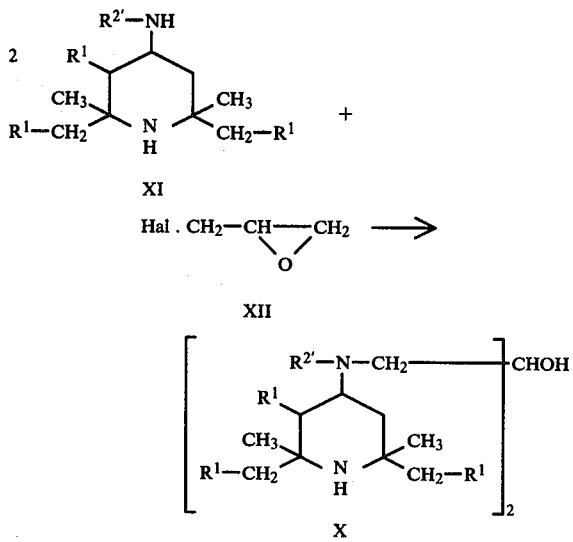

(in which $R^1$, $R^{2'}$ and Hal are as defined above). The reaction may be carried out under similar conditions to those employed in Method 2.

METHOD 5

Compounds in which Y and Z represent hydrogen atoms and $R^2$ represents an acyl group may be prepared by reacting a corresponding compound in which $R^2$ represents a hydrogen atom, and which may have been obtained by either of foregoing Methods 1 and 2, with an acid halide or anhydride of the corresponding carboxylic acid.

When an acid halide is used, the reaction is advantageously carried out in the presence of an inert organic solvent and preferably also in the presence of an acid-binding agent. There is no particular limitation upon the nature of the solvent employed, provided that it has no adverse effect upon the reaction. Examples of suitable solvents include: aromatic hydrocarbons, such as benzene, toluene and xylene; halogenated aliphatic hydrocarbons, such as chloroform and trichloroethane; and ethers, such as diethyl ether, tetrahydrofuran and dioxane. Where an acid-binding agent is employed, preferred examples include: alkali metal hydroxides, such as sodium hydroxide and potassium hydroxide; alkali metal carbonates, such as sodium carbonate and potassium carbonate; and organic bases, particularly amines, such as triethylamine and pyridine. The reaction may suitably be carried out at a temperature from about 0° C. to about 130° C.

When an acid anhydride is used, the reaction is preferably carried out either in the presence of an inert organic solvent or in the absence of such a solvent but using a stoichiometric excess of the acid anhydride. There is no particular limitation upon the nature of the solvent, if employed, provided that it has no adverse effect upon the reaction. Examples of suitable solvents include: aromatic hydrocarbons, such as benzene, toluene and xylene; and ethers, such as dioxane, tetrahydrofuran and diethylene glycol dimethyl ether. The reaction is usually and conveniently carried out at a temperature which may range from ambient temperature to about 160° C.

METHOD 6

Compounds in which Y and Z both represent hydrogen atoms and $R^2$ represents an alkylsulphonyl group or an optionally substituted phenylsulphonyl group may be obtained by reacting the corresponding compound in which $R^2$ represents a hydrogen atom, which can have been produced by either of foregoing Methods 1 and 2, with the corresponding sulphonyl chloride.

The reaction is suitably carried out under similar conditions to those described in above Method 5 when employing an acid halide.

METHOD 7

Compounds in which Y and Z both represent hydrogen atoms and $R^2$ represents a group of formula —CONHR$^3$ (in which $R^3$ is as defined above) may be obtained by reacting the corresponding compound in which $R^2$ represents a hydrogen atom, which can have been produced by either of foregoing Methods 1 and 2, with an isocyanate of formula $R^3NCO$.

The reaction may be performed in the presence or the absence of an inert organic solvent. Where a solvent is employed, its nature is not critical, provided that it has no adverse effect upon the reaction. Examples of suitable solvents include: aromatic hydrocarbons, such as benzene, toluene and xylene; and ethers, such as tetrahydrofuran and dioxane. The reaction is usually and preferably carried out at a temperature which may range from about 50° C. to about 130° C.

It should be noted that, particularly when an excess of reagent is employed in Methods 5 and 7 above, compounds in which both $R^2$ and Z are identical acyl groups or groups of formula —CONHR$^3$ may be obtained. Furthermore, if an excess of acid anhydride is used as the reagent in Method 5, compounds in which all of $R^2$, Z and Y represent identical aliphatic acyl groups may be obtained.

METHOD 8

Compounds in which $R^2$ and Z both represent hydrogen atoms and Y represents an alkyl group, an alkenyl group or a benzyl group may be obtained by reacting a compound corresponding to the compound of formula (IV), previously defined, but in which the nitrogen atom at the 1-position is substituted by an alkyl, alkenyl or benzyl group corresponding to the desired group Y, following the procedure of either Method 1 or 2.

METHOD 9

Compounds of formula (I) in which Y represents a hydrogen atom, $R^2$ represents a group other than a hydrogen atom and Z represents an alkyl group, an allyl group or a benzyl group may be prepared by reacting the corresponding compound in which Z represents a hydrogen atom, which can have been obtained in any of Methods 3, 4, 5, 6 and 7, with the corresponding halogen compound of the group Z which it is desired to introduce.

This reaction may be carried out by reacting a compound in which Z represents a hydrogen atom first with a strongly basic alkali metal compound (such as sodium hydride or potassium t-butoxide) and then with the halogen compound in the presence of an inert organic solvent. There is no particular limitation upon the nature of the solvent employed, provided that it has no adverse effect upon the reaction. Examples of suitable solvents include: aromatic hydrocarbons, such as benzene, toluene and xylene; ethers, such as tetrahydrofuran and dioxane; and amides, such as N,N-dimethylformamide, N,N-dimethylacetamide and hexamethylphosphoric triamide. The reaction is usually and conveniently carried out by heating the reagents at a temperature of from about 50° C. to about 120° C.

METHOD 10

Compounds in which Y represents a hydrogen atom, $R^2$ represents a group other than a hydrogen atom and Z represents an acyl group may be obtained by reacting the corresponding compound in which Z represents a hydrogen atom, which may have been obtained by any of Methods 3, 4, 5, 6 and 7 described above, with an active derivative of a carboxylic acid (e.g. an acid halide, acid anhydride or lower alkyl ester of the acid) corresponding to the desired acyl group.

When a lower alkyl ester of the acid is used, the reaction is preferably carried out in the presence of an inert organic solvent and in the presence of a strong base. There is no particular limitation on the nature of the solvent employed and examples of suitable solvents include: aromatic hydrocarbons, such as benzene, toluene and xylene; and aliphatic hydrocarbons, such as n-heptane, n-octane or isooctane. Examples of suitable strong bases include: strongly basic alkali metal compounds, such as sodium methoxide, sodium ethoxide, potassium hydroxide and lithium amide; and titanic acid compounds, such as tetraisopropyl titanate and tetrabutyl titanate. The reaction is preferably carried out by heating the reagents at a temperature from about 80° C. to about 180° C.

When an acid halide or acid anhydride is used, the reaction may be carried out under conditions similar to those described in Method 5.

If an excess of acid halide or acid anhydride, particularly of acid anhydride is used, compounds in which Y and Z are identical acyl groups may be obtained.

METHOD 11

Compounds in which Y represents a hydrogen atom, $R^2$ represents a group other than a hydrogen atom and Z represents a group of formula —CONHR$^9$ (wherein $R^9$ is as defined above) may be prepared by reacting the corresponding compound in which Z represents a hydrogen atom, and which may have been obtained by any of foregoing Methods 3, 4, 5, 6 and 7, with an isocyanate of formula $R^9NCO$ following the procedure described in Method 7.

METHOD 12

Compounds in which Z represents a hydrogen atom, $R^2$ represents a group other than a hydrogen atom and Y represents an alkyl group, an alkenyl group, a benzyl group, a 2,3-epoxypropyl group, a group of formula

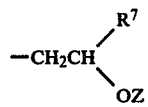

(in which $R^7$ is as defined above) or a group of formula —$CH_2COOR^8$ (in which $R^8$ is as defined above) may be obtained by reacting the corresponding compound in which Y represents a hydrogen atom, and which can have been obtained by any of foregoing Methods 3 to 7) with the corresponding halo compound of formula Y"Hal, in which Y" represents an alkyl group, an alkenyl group, a benzyl group, a 2,3-epoxypropyl group, a group of formula

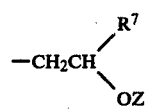

or a group of formula —$CH_2COOR^8$, and Hal is as defined above.

This reaction may be carried out in the presence or absence of an inert organic solvent. Where a solvent is employed, its nature is not critical provided that it has no adverse effect upon the reaction. Examples of suitable solvents include: aromatic hydrocarbons, such as benzene, toluene and xylene; chlorinated hydrocarbons, such as chloroform, trichloroethane and chlorobenzene; and amides, such as N,N-dimethylformamide, N,N-dimethylacetamide and hexamethylphosphoric triamide. The reaction is suitably carried out at a temperature which may vary from about ambient temperature to about 180° C.

METHOD 13

Compounds in which Z represents a hydrogen atom, $R^2$ represents an acyl group, an alkylsulphonyl group, an optionally substituted phenylsulphonyl group or a group of formula —$CONHR^3$ (in which $R^3$ is as defined above) and Y represents an alkyl group, an alkenyl group or a benzyl group may also be prepared by reacting the corresponding compound in which $R^2$ and Z both represent hydrogen atoms and Y represents an alkyl group, an alkenyl group or a benzyl group (which can have been produced by foregoing Method 8) in accordance with the procedures described in Methods 5, 6 and 7.

METHOD 14

As a further alternative, compounds in which Z represents a hydrogen atom, $R^2$ represents an alkyl group, a cycloalkyl group, an optionally substituted phenyl group, a naphthyl group, an aralkyl group or a 2-hydroxyethyl group and Y represents an alkyl group, an alkenyl group or a benzyl group may be prepared following the procedure of Methods 1 or 2 but employing, in place of the compound of formula (IV), a corresponding compound in which the amino group at the 4-position is substituted by the desired group $R^2$.

METHOD 15

Compounds in which Z represents a hydrogen atom, $R^2$ represents a group other than a hydrogen atom and Y represents an aliphatic acyl group or a group of formula

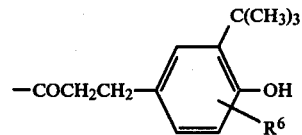

(in which $R^6$ is as defined above) may be prepared by first protecting the hydroxy group or groups of the corresponding compound in which Y represents a hydrogen atom (and which can have been obtained by any of foregoing Methods 3 to 7), e.g. by benzylation, after which the compound is reacted with an acid halide of a carboxylic acid having the desired acyl group or having the desired group of formula

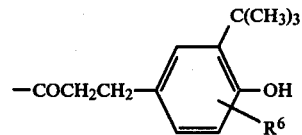

and finally removing the protecting group or groups. In place of the acid halide, the corresponding anhydride may be used. The reaction may be carried out in the presence of an inert organic solvent or in the absence of such a solvent but using an excess of the acid halide or anhydride. Where a solvent is employed, there is no particular limitation upon its nature, provided that it does not interfere with the reaction. Examples of suitable solvents include: aromatic hydrocarbons, such as benzene, toluene and xylene; and ethers, such as dioxane, tetrahydrofuran and diethylene glycol dimethyl ether. The reaction is conveniently and preferably carried out at a temperature which may range from ambient temperature to about 160° C.

METHOD 16

Compounds of which all of $R^2$, Y and Z represent groups other than hydrogen atoms may be prepared by introducing a substituent Z" (in which Z" is any of the groups defined for Z other than a hydrogen atom) into a compound in which $R^2$ and Y represent groups other than hydrogen atoms and Z represents a hydrogen atom (which compounds may be obtained by any of Methods 12 to 15) following any of the procedures described in Methods 9, 10 and 11. In particular, when a compound in which Z represents a hydrogen atom and $R^2$ represents a 2-hydroxyethyl group and/or Y represents a group of formula —$CH_2CH(OH)R^7$ (in which $R^7$ is as defined above) is reacted with an excess of reagent following the procedure of any of Methods 9 to 11, the hydrogen atom represented by Z in the starting compound is replaced by the appropriate substituent simultaneously with the introduction of that substituent into the above-mentioned hydroxy groups.

METHOD 17

Compounds in which all of $R^2$, Y and Z represent groups other than hydrogen atoms may also be prepared by introducing a substituent Y''' (in which Y''' is any of the groups defined for Y except a hydrogen atom) into a corresponding compound in which Y represents a hydrogen atom and $R^2$ and Z are groups other than hydrogen atoms (which compound may be obtained by any of Methods 12 to 15) using the procedure described in any of foregoing Methods 9 to 11.

METHOD 18

Compounds of formula (I) in which Z represents a lower alkyl group, particularly methyl or ethyl, may also be prepared by reacting a corresponding compound in which Z represents a hydrogen atom with a dialkyl sulphate. If both Y and Z in the compound used as starting material represent hydrogen atoms, then compounds in which both Y and Z represent the same lower alkyl group are generally obtained. This reaction may be carried out in the presence or absence of an inert organic solvent. Where a solvent is used, its nature is not critical, provided that it has no adverse effect upon the reaction. Examples of suitable solvents include: aromatic hydrocarbons, such as benzene or xylene; ethers, such as dioxane and tetrahydrofuran; lower aliphatic ketones, such as acetone; and mixtures of any of these solvents with water. The reaction is advantageously carried out in the presence of an alkali metal hydroxide (for example sodium hydroxide or potassium hydroxide) or in the presence of an alkali metal carbonate (such as potassium carbonate). The reaction is conveniently and preferably carried out at a temperature which may range from about ambient temperature to about 150° C.

METHOD 19

Compounds of formula (I) in which $R^2$ represents a group other than a hydrogen atom, Z is as defined above and Y represents a methyl group may also be obtained by reacting the corresponding compound in which Y represents a hydrogen atom with formic acid and formaldehyde by means of the known Leuckart-Wallach reaction. If a compound in which both Y and $R^2$ represent hydrogen atoms is used as the starting material, the product may be or may contain a compound in which both Y and $R^2$ represent methyl groups.

METHOD 20

Compounds of formula (I) in which $R^2$ represents a group other than a hydrogen atom, Z is as defined above and Y represents a group of formula —CH$_2$CH(OH)R$^7$ (in which $R^7$ is as defined above) may also be prepared by reacting the corresponding compound in which Y represents a hydrogen atom with ethylene oxide, propylene oxide or styrene oxide. If a compound in which both Y and $R^2$ represent hydrogen atoms is reacted with ethylene oxide, compounds in which both Y and $R^2$ represent 2-hydroxyethyl groups may be obtained. The reaction is preferably carried out in the presence of a solvent. Where a solvent is used, its nature is not critical, provided that it has no adverse effect upon the reaction. Examples of suitable solvents are alcohols, such as methanol, ethanol or propanol. The reaction is preferably carried out in the presence of an acidic catalyst, for example sulphuric acid or hydrochloric acid. The reaction temperature is preferably from about 60° C. to about 160° C.

The hydroxy compounds thus obtained may be converted to the desired esters or ethers by further introduction of a substituent Z" (in which Z" is as defined above).

Acid addition salts of compounds of formula (I) may be prepared by neutralizing a compound of formula (I) with a suitable acid, preferably in an inert organic solvent or in a mixture thereof with water. Such a procedure is well-known to those skilled in the art.

The polyalkylated 4-amino piperidine derivatives of formula (I) and their acid addition salts are useful for stabilizing a wide range of synthetic polymers against the deterioration caused by heat and/or light. They are highly effective stabilizers and are less volatile on the application of heat than are conventional piperidine derivatives used as light stabilizers. Accordingly, the invention further provides a polymeric composition comprising a polymer and, as stabilizer, a piperidine derivative of formula (I) or an acid addition salt thereof.

Synthetic polymers which can be stabilized in this way include:

olefin and diene polymers including homopolymers of olefins and dienes (e.g. low density, high density and cross-linked polyethylenes, polypropylene, polyisobutylene, polymethylbutene-1, polymethylpentene-1, polyisoprene and polybutadiene); mixtures of such homopolymers (e.g. mixtures of polypropylene with polyethylene, polypropylene with polybutene-1 or polypropylene with polyisobutylene); and copolymers of olefins and dienes (e.g. ethylene/propylene copolymers, propylene/butene-1 copolymers, propylene/isobutylene copolymers, ethylene/butene-1 copolymers and terpolymers of ethylene and propylene with such dienes as hexadiene, dicyclopentadiene or ethylidenenorbornene);

styrene polymers including polystyrene, copolymers of styrene and of α-methylstyrene (e.g. styrene/butadiene copolymers, styrene/acrylonitrile copolymers, styrene/acrylonitrile/methyl methacrylate copolymers, styrene/acrylonitrile/acrylic ester copolymers, styrene/acrylonitrile copolymers modified with acrylic ester polymers to provide impact strength, and styrene polymers modified with ethylene/propylene/diene elastomers to provide impact strength); and graft copolymers of styrene (e.g. polymers in which styrene is grafted onto polybutadiene and polymers in which styrene and acrylonitrile are grafted onto polybutadiene, as well as mixtures thereof with the aforementioned styrene copolymers—commonly known as acrylonitrile/butadiene/styrene or "ABS" plastics);

halogenated vinyl and vinylidene polymers including polyvinyl chloride, polyvinylidene chloride, polyvinyl fluoride, polychloroprene, chlorinated rubbers, vinyl chloride/vinylidene chloride copolymers, vinyl chloride/vinyl acetate copolymers and vinylidene chloride/vinyl acetate copolymers;

polymers derived from α,β-unsaturated acids and derivatives thereof, including polyacrylates and polymethacrylates, polyacrylic amides and polyacrylonitrile;

polymers derived from unsaturated alcohols and amines and from the acyl derivatives thereof or acetals, including polyvinyl alcohol, polyvinyl acetate, polyvinyl stearate, polyvinyl benzoate, polyvinyl maleate, polyvinyl butyral, polyallyl phthalate and polyallyl melamine, and copolymers thereof with other ethylenically unsaturated monomers (e.g. ethylene/vinyl acetate copolymers);

epoxy polymers including homopolymers and copolymers derived from epoxides (e.g. polyethylene oxide) and polymers derived from bis-glycidyl ethers;

polyacetals, polyalkylene oxides and polyphenylene oxides including polyoxymethylene, oxymethylene/ethylene oxide copolymers, polyoxyethylene, polypropylene oxide, polyisobutylene oxide and polyphenylene oxides;
polyurethanes and polyureas
polycarbonates
polysulphones
polyamides and copolyamides
derived from diamines and dicarboxylic acids and/or from amino-carboxylic acids or their corresponding lactams, including nylon-6, nylon-6,6, nylon-6,10, nylon-11 and nylon-12;
polyesters
derived from dicarboxylic acids and dialcohols and/or from hydroxy-carboxylic acids and their corresponding lactones, e.g. polyethylene glycol terephthalate and poly-1,4-dimethylolcyclohexane terephthalate;
cross-linked polymers
derived from aldehydes together with phenols, ureas or melamines, e.g. phenol/formaldehyde, urea/formaldehyde and melamine/formaldehyde resins;
alkyd resins
e.g. glycerol/phthalic acid resins and mixtures thereof with melamine/formaldehyde resins;
unsaturated polyester resins
derived from copolyesters of saturated and unsaturated dicarboxylic acids with polyhydric alcohols as well as from vinyl compounds as cross-linking agents, and also halogenated flame-resistant modifications thereof.

The amount of the stabilizer of the invention needed for effective stabilization of a synthetic polymer will depend upon a variety of factors, including the type and properties of the polymer concerned, its intended use and the presence, if any, of other stabilizers. It is generally satisfactory to use from 0.01% to 5% by weight of the stabilizer of the invention, based on the weight of the polymer, but the most effective range will vary with the type of polymer; viz from 0.01% to 2%, preferably from 0.02% to 1.0%, by weight for olefin, diene and styrene polymers; from 0.01% to 1.0%, preferably from 0.02% to 0.5%, by weight for vinyl and vinylidene polymers; and from 0.01% to 5.0%, preferably from 0.02%, to 2.0% by weight for polyurethanes and polyamides. If desired, two or more of the stabilizers of the invention may be used together.

The stabilizers of the invention may readily be incorporated into synthetic polymers by conventional techniques at any convenient stage prior to the manufacture of shaped articles therefrom. For example, the stabilizer may be mixed with the polymer in dry powder form, or a suspension or emulsion of the stabilizer may be mixed with a solution, suspension or emulsion of the polymer.

The stabilized polymeric compositions of the invention may optionally also contain one or more of various additives conventionally used in polymer technology, such as the additives listed in British Pat. No. 1,401,924, at pages 11–13, the disclosure of which is hereby incorporated by reference.

The invention is further illustrated by the following non-limiting Examples, in which all parts are by weight,

EXAMPLE 1

2,2-Bis[4-{3-[N-butyl-N-(2,2,6,6-tetramethyl-4-piperidyl)amino]-2-hydroxypropoxy}phenyl]propane (Compound No. 70)

To 150 ml of methanol were added 21.2 g of 4-butylamino-2,2,6,6-tetramethylpiperidine and 17.0 g of 2,2-bis[p-(2,3-epoxypropoxy)phenyl]propane; the mixture was then refluxed, with stirring, for 5 hours. After completion of the reaction, the solvent was removed from the reaction mixture by evaporation under reduced pressure, and the resulting residue was purified by column chromatography through silica gel eluted with a 5:1 by volume mixture of ethyl acetate and triethylamine. The desired compound was obtained in the form of a white powder having an $R_f$ value of 0.63 on thin layer chromatography on silica gel developed with a 5:1 by volume mixture of ethyl acetate and triethylamine.

EXAMPLE 2

2,2-Bis[4-{2-hydroxy-3-[(2,2,6,6-tetramethyl-4-piperidyl)amino]propoxy}phenyl]propane (Compound No. 16)

To 100 ml of methanol were added 7.8 g of 4-amino-2,2,6,6-tetramethylpiperidine and 8.5 g of 2,2-bis[p-(2,3-epoxypropoxy)phenyl]propane; the mixture was then reacted in a similar manner to that described in Example 1, giving the desired compound in the form of a white powder. The compound had an $R_f$ value of 0.28 on thin layer chromatography on silica gel developed with a 1:3:1 by volume mixture of methanol, ethyl acetate and triethylamine.

EXAMPLE 3

2,2-Bis[4-{2-hydroxy-3-[N-methyl-N-(2,2,6,6-tetramethyl-4-piperidyl)amino]propoxy}phenyl]propane (Compound No. 21)

To 50 ml of methanol were added 3.4 g of 2,2,6,6-tetramethyl-4-methylaminopiperidine and 3.4 g of 2,2-bis[p-(2,3-epoxypropoxy)phenyl]propane; the mixture was then reacted in a manner similar to that described in Example 1, giving the desired compound in the form of a white powder. The compound had an $R_f$ value of 0.50 on thin layer chromatography on silica gel developed with a 1:3:1 by volume mixture of methanol, ethyl acetate and triethylamine.

EXAMPLE 4

2,2-Bis[4-{2-hydroxy-3-[(1,2,2,6,6-pentamethyl-4-piperidyl)amino]propoxy}phenyl]propane (Compound No. 17)

To 100 ml of methanol were added 12 g of 4-amino-1,2,2,6,6-pentamethylpiperidine and 11 g of 2,2-bis[p-(2,3-epoxypropoxy)phenyl]propane; the mixture was then reacted in a similar manner to that described in Example 1, giving the desired compound in the form of white crystals melting at 141°–143° C. The compound had an $R_f$ value of 0.64 on thin layer chromatography on silica gel developed with a 1:3:1 by volume mixture of methanol, ethyl acetate and triethylamine.

EXAMPLE 5

2,2-Bis[4-{3-[N-butyl-N-(1,2,2,6,6-pentamethyl-4-piperidyl)amino]-2-hydroxypropoxy}phenyl]propane (Compound No. 71)

10 g of 2,2-bis[4-{3-[N-butyl-N-(2,2,6,6-tetramethyl-4-piperidyl)amino]-2-hydroxypropoxy}phenyl]propane obtained as described in Example 1, were added to a mixture of 80 ml of formic acid and 60 ml of 37% w/w formalin; the mixture was then refluxed for 5 hours. At the end of this time, the reaction mixture was made alkaline by the addition of a 10% w/w aqueous solution of potassium carbonate and then extracted with 100 ml of benzene. The extract was washed with a 10% w/w aqueous solution of potassium carbonate and then dried over anhydrous potassium carbonate.

The residue obtained by removing the solvent from the extract by evaporation under reduced pressure was purified by column chromatography through silica gel eluted with a 8:16:1 by volume mixture of ethyl acetate, benzene and triethylamine. The desired compound was obtained in the form of a white powder having an $R_f$ value of 0.66 on thin layer chromatography on silica gel developed with a 8:8:1 by volume mixture of ethyl acetate, diethyl ether and triethylamine.

EXAMPLE 6

2,2-Bis[4-{3-[N-(1-allyl-2,2,6,6-tetramethyl-4-piperidyl)-N-butylamino]2-hydroxypropoxy}phenyl]propane (Compound No. 73)

10 g of 2,2-bis[4-{3-[N-butyl-N-(2,2,6,6-tetramethyl-4-piperidyl)amino]-2-hydroxypropoxy}phenyl]propane, obtained as described in Example 1, were added to 40 g of allyl bromide; the mixture was then refluxed, with stirring, for 4 hours. At the end of this time, the mixture was made alkaline by the addition of a 10% w/w aqueous solution of potassium carbonate and then extracted with benzene. The extract was washed with water and dried over anhydrous potassium carbonate. The solvent was removed from the extract by evaporation under reduced pressure and then the residue thus obtained was purified by column chromatography through silica gel eluted with a 20:1 by volume mixture of ethyl acetate and triethylamine. The desired compound was obtained in the form of a pale yellow powder having an $R_f$ value of 0.66 on thin layer chromatography on silica gel developed with a 4:1 by volume mixture of ethyl acetate and methanol.

EXAMPLE 7

2,2-Bis[4-{2-hydroxy-3-[N-methyl-N-(1,2,2,6,6-pentamethyl-4-piperidyl)amino]propoxy}phenyl]propane (Compound No. 22)

10 g of 2,2-bis[4-{2-hydroxy-3-[(1,2,2,6,6-pentamethyl-4-piperidyl)amino]propoxy}phenyl]propane, obtained as described in Example 4, were added to a mixture of 30 g of formic acid and 30 g of 37% w/w formalin; the mixture was then reacted in a similar manner to that described in Example 5, giving the desired compound in the form of a white powder. The compound had an $R_f$ value of 0.73 on thin layer chromatography on silica gel developed with a 9:1 by volume mixture of ethyl acetate and triethylamine.

EXAMPLE 8

2,2-Bis[4-{2-acetoxy-3-[N-(1-acetyl-2,2,6,6-tetramethyl-4-piperidyl)-N-butylamino]propoxy}phenyl]propane (Compound No. 90)

A mixture of 5 g of 2,2-bis[4-{3-[N-butyl-N-(2,2,6,6-tetramethyl-4-piperidyl)amino]2-hydroxypropoxy}phenyl]propane, obtained as described in Example 1, and 20 ml of acetic anhydride in 50 ml of benzene was refluxed, with stirring, for 5 hours. At the end of this time, a 10% w/w aqueous solution of potassium carbonate was added to the reaction mixture and the benzene layer was separated off, washed with water and then dried over anhydrous potassium carbonate. The residue obtained by removing the solvent from the benzene solution was purified by column chromatography on silica gel eluted with a 4:1 by volume mixture of ethyl acetate and benzene. The desired compound was obtained in the form of a pale brown powder having an $R_f$ value of 0.90 on thin layer chromatography on silica gel developed with a 1:9 by volume mixture of methanol and ethyl acetate.

EXAMPLE 9

2,2-Bis[4-{2-acetoxy-3-[N-(1,2,2,6,6-pentamethyl-4-piperidyl)acetamido]propoxy}phenyl]propane (Compound No. 149)

A mixture of 1 g of 2,2-bis[4-{2-hydroxy-3-[(1,2,2,6,6-pentamethyl-4-piperidyl)amino]propoxy}phenyl]propane, obtained as described in Example 4, and 1 g of acetic anhydride in 10 ml of benzene was reacted in a similar manner to that described in Example 8, giving the desired compound in the form of a white powder. The compound had an $R_f$ value of 0.70 on thin layer chromatography on silica gel developed with a 9:1 by volume mixture of ethyl acetate and triethylamine.

EXAMPLE 10

2-Hydroxy-1,3-bis[N-methyl-N-(2,2,6,6-tetramethyl-4-piperidyl)amino]propane (Compound No. 239)

A mixture of 2.2 g of 4-[N-(2,3-epoxypropyl)-N-methylamino]-2,2,6,6-tetramethylpiperidine and 1.7 g of 4-methylamino-2,2,6,6-tetramethylpiperidine in 20 ml of benzene was refluxed, with stirring, for 3 hours. At the end of this time, the solvent was removed from the reaction mixture by evaporation under reduced pressure and then the resulting residue was distilled in vacuo, giving the desired compound in the form of a colourless, viscous oil boiling at 194°–196° C. at 0.2 mmHg.

EXAMPLE 11

2-Hydroxy-1,3-bis[(2,2,6,6-tetramethyl-4-piperidyl)amino]propane (Compound No. 237)

To 200 ml of diethyl ether were added 15.6 g of 4-amino-2,2,6,6-tetramethylpiperidine and 14 g of anhydrous potassium carbonate. A solution of 10.9 g of 1,3-dibromo-2-propanol in 50 ml of diethyl ether was then added dropwise to the mixture, at ambient temperature. When the addition was complete, the mixture was refluxed for 8 hours. At the end of this time, the reaction mixture was cooled and then washed with, in turn, a 20% w/w aqueous solution of potassium hydroxide and water. The mixture was then dried over anhydrous potassium carbonate and then the solvent was removed by evaporation under reduced pressure. The residue was distilled in vacuo, giving the desired compound in the form of a colourless, very viscous product boiling at 184°–185° C. at 0.01 mmHg.

EXAMPLE 12

2-Hydroxy-1,3-bis[N-octyl-N-(2,2,6,6-tetramethyl-4-piperidyl)amino]propane (Compound No. 252)

To 150 ml of methanol were added 13.4 g of 2,2,6,6-tetramethyl-4-octylaminopiperidine and 5.0 g of anhydrous potassium carbonate. 3.4 g of epibromohydrin were then slowly added dropwise to the mixture to ambient temperature. When the addition was complete, the reaction mixture was heated at 50°–55° C., with stirring, for 2 hours and then refluxed for 5 hours. At the end of this time, the solvent was evaporated from the reaction mixture under reduced pressure and the residue thus obtained was dissolved in 250 ml of benzene. This benzene solution was washed with, in turn, a 20% w/w aqueous solution of potassium hydroxide and water, and then dried over anhydrous potassium carbonate. The solvent was then removed from the solution and the residue was distilled in vacuo, giving the desired compound in the form of a pale yellow, transparent liquid boiling at 212°–214° C. at $1.5 \times 10^{-3}$ mmHg.

EXAMPLE 13

2-Acetoxy-1,3-bis[N-(1-acetyl-2,2,6,6-tetramethyl-4-piperidyl)acetamido]propane (Compound No. 255)

A mixture of 5 g of 2-hydroxy-1,3-bis[(2,2,6,6-tetramethyl-4-piperidyl)amino]propane, obtained as described in Example 11, with 100 ml of acetic anhydride was refluxed, with stirring, for 4 hours. At the end of this time, the mixture was condensed by evaporation in vacuo, leaving a residue which was then dissolved in 200 ml of benzene. This benzene solution was washed with, in turn, a 5% w/w aqueous solution of sodium carbonate and water. The residue obtained by removing the solvent from the benzene solution was purified by column chromatography through silica gel eluted with a 20:4:2:1 by volume mixture of ethyl acetate, benzene, ethanol and triethylamine, giving crude crystals. These crystals were recrystallized from a 5:1 by volume mixture of n-hexane and benzene, giving the desired compound in the form of white crystals melting at 152°–153° C.

EXAMPLE 14

1,2-Bis{3-[N-butyl-N-(2,2,6,6-tetramethyl-4-piperidyl)amino]-2-hydroxypropoxy}ethane (Compound No. 4)

A mixture of 6.4 g of 4-butylamino-2,2,6,6-tetramethylpiperidine and 2.6 g of ethylene glycol bis(2,3-epoxypropyl)ether in 50 ml of methanol was refluxed, with stirring for 5 hours. At the end of this time, the solvent was removed from the reaction mixture by evaporation under reduced pressure and then the residue was recrystallized from n-hexane, giving the desired compound in the form of white crystals melting at 81°–83° C. and boiling at 258°–262° C. at 0.06 mmHg.

EXAMPLE 15

1,2-Bis{3-[N-butyl-N-(1,2,2,6,6-pentamethyl-4-piperidyl)amino]-2-hydroxypropoxy}ethane (Compound No. 5)

8 g of 1,2-bis{3-[N-butyl-N-(2,2,6,6-tetramethyl-4-piperidyl)amino]-2-hydroxypropoxy}ethane, obtained as described in Example 14, were added to a mixture of 20 g of formic acid and 20 g of 37% w/w formalin. The mixture was then reacted in a manner similar to that described in Example 5, giving a crude product. This product was purified by distillation in vacuo, giving the desired compound in the form of a colourless, viscous oil boiling at 266°–269° C. at 0.02 mmHg.

EXAMPLE 16

2,2-Bis[4-{2-hydroxy-3-[N-octyl-N-(2,2,6,6-tetramethyl-4-piperidyl)amino]propoxy}phenyl]propane (Compound No. 98)

A mixture of 13 g of 2,2,6,6-tetramethyl-4-octylaminopiperidine and 8 g of 2,2-bis[p-(2,3-epoxypropoxy)phenyl]propane in 200 ml of methanol was refluxed, with stirring, for 6 hours. At the end of this time, the solvent was removed from the residue by evaporation under reduced pressure, leaving a residue, which was purified by column chromatography through silica gel eluted with a 20:4:2:1 by volume mixture of ethyl acetate, benzene, ethanol and triethylamine. The desired compound was obtained in the form of a colourless, transparent, very viscous liquid having an $R_f$ value of 0.27 on thin layer chromatography on silica gel developed with a 20:4:2:1 by volume mixture of ethyl acetate, benzene, ethanol and triethylamine.

EXAMPLE 17

2,2-Bis[4-{2-hydroxy-3-[N-(2-hydroxyethyl)-N-(2,2,6,6-tetramethyl-4-piperidyl)amino]propoxy}phenyl]propane (Compound No. 172)

A mixture of 20 g of 4-[(2-hydroxyethyl)amino]-2,2,6,6-tetramethylpiperidine and 17 g of 2,2-bis[p-(2,3-epoxypropoxy)phenyl]propane in 300 ml of methanol was reacted in a manner similar to that described in Example 16, giving the desired compound in the form of a colourless, vitreous mass, melting at 69°–71° C. The compound had an $R_f$ value of 0.30 on thin layer chromatography on silica gel developed with a 10:2:5:2 by volume mixture of ethyl acetate, benzene, ethanol and triethylamine.

EXAMPLE 18

Bis{3-[N-butyl-N-(2,2,6,6-tetramethyl-4-piperidyl)amino]-2-hydroxypropyl}1,2-cyclohexanedicarboxylate (Compound No. 227)

A mixture of 5 g of 4-butylamino-2,2,6,6-tetramethylpiperidine and 3 g of bis(2,3-epoxypropyl)1,2-cyclohexanedicarboxylate in 10 ml of t-butanol was refluxed, with stirring, for 8 hours. At the end of this time, the solvent was removed from the reaction mixture by evaporation under reduced pressure and the resulting residue was purified by column chromatography through silica gel eluted with a 20:1 by volume mixture of ethyl acetate and triethylamine. The desired compound was obtained in the form of a pale yellow, viscous oil having an $R_f$ value of 0.53 on thin layer chromatography on silica gel developed with a 5:1 by volume mixture of ethyl acetate and triethylamine.

EXAMPLE 19

Bis{3-[N-butyl-N-(2,2,6,6-tetramethyl-4-piperidyl)amino]-2-phenylcarbamoyloxypropyl}1,2-cyclohexanedicarboxylate (Compound No. 232)

A mixture of 2.4 g of bis{3-[N-butyl-N-(2,2,6,6-tetramethyl-4-piperidyl)amino]-2-hydroxypropyl}1,2-cyclohexanedicarboxylate, obtained as described in Example 18, and 2.4 g of phenylisocyanate in 30 ml of benzene was refluxed, with stirring, for 3 hours. At the end of this time, the solvent was removed from the reaction mixture by evaporation under reduced pressure and the resulting residue was purified by column chromatography through silica gel eluted with a 20:1 by volume mixture of ethyl acetate and triethylamine. The desired compound was obtained in the form of a vitreous mass having an $R_f$ value of 0.58 on thin layer chromatography on silica gel developed with a 5:1 by volume mixture of ethyl acetate and triethylamine.

EXAMPLE 20

2,2-Bis[4-{2-hydroxy-3-[N-octyl-N-(1,2,2,6,6-pentamethyl-4-piperidyl)amino]propoxy}phenyl]propane (Compound No. 99)

To a mixture of 30 g of formic acid and 30 g of 37% w/w formalin were added 10 g of 2,2-bis[4-{2-hydroxy-3-[N-octyl-N-(2,2,6,6-tetramethyl-4-piperidyl)amino]propoxy}phenyl]propane, obtained as described in Example 16. The mixture was then reacted following a procedure similar to that described in Example 5, giving a crude product. This product was purified by column chromatography through silica gel eluted with a 19:1 by volume mixture of ethyl acetate and triethylamine. The desired compound was obtained in the form of a colourless, viscous oil having an $R_f$ value of 0.58 on thin layer chromatography on silica gel developed with a 19:1 by volume mixture of ethylacetate and triethylamine.

EXAMPLE 21

2,2-Bis[4-{2-methoxy-3-[N-octyl-N-(1,2,2,6,6-pentamethyl-4-piperidyl)amino]propoxy}phenyl]propane (Compound No. 108)

To 20 ml of tetrahydrofuran were added 1.5 g of 2,2-bis[4-{2-hydroxy-3-[N-octyl-N-(1,2,2,6,6-pentamethyl-4-piperidyl)amino]propoxy}phenyl]propane. To this mixture were then added, with stirring, 3 ml of a 15% w/w solution of butyllithium in n-hexane, and the mixture was refluxed for 1 hour. The reaction mixture was then cooled to ambient temperature and there were added 0.76 g of methyl iodide; the mixture was then refluxed for 3 hours. At the end of this time, water was added to the reaction mixture and the organic phase was separated and dried over anhydrous potassium carbonate. The solvent was removed from the organic phase by evaporation under reduced pressure and the resulting residue was purified by column chromatography through silica gel eluted with a 19:1 by volume mixture of ethyl acetate and triethylamine. The desired compound was obtained in the form of a pale yellow, viscous oil having an $R_f$ value of 0.74 on thin layer chromatography on silica gel developed with a 19:1 by volume mixture of ethyl acetate and triethylamine.

EXAMPLE 22

2,2-Bis[4-{2-lauroyloxy-3-[N-octyl-N-(1,2,2,6,6-pentamethyl-4-piperidyl)amino]propoxy}phenyl]propane (Compound No. 112)

A mixture of 1.5 g of 2,2-bis[4-{2-hydroxy-3-[N-octyl-N-(1,2,2,6,6-pentamethyl-4-piperidyl)amino]propoxy}phenyl]propane, obtained as described in Example 20, and 3.6 g of lauric anhydride in 5 ml of xylene was refluxed, with stirring, for 7 hours. At the end of this time, 100 ml of benzene were added to the reaction mixture, and the mixture was then washed with, in turn, a 10 w/w aqueous solution of potassium carbonate and water, and then dried over anhydrous magnesium carbonate. The solvent was removed from the benzene solution by evaporation under reduced pressure and the residue thus obtained was purified by column chromatography through silica gel eluted with a 40:1 by volume mixture of ethylacetate and triethylamine. The desired compound was obtained in the form of a colourless oil having an $R_f$ value of 0.74 on thin layer chromatography on silica gel developed with a 40:1 by volume mixture of ethylacetate and triethylamine.

EXAMPLE 23

2,2-Bis[4-{2-benzyloxy-3-[N-(2-benzyloxyethyl)-N-(2,2,6,6-tetramethyl-4-piperidyl)amino]propoxy}phenyl]propane (Compound No. 177)

A mixture of 7.4 g of 2,2-bis[4-{2-hydroxy-3-[N-(2-hydroxyethyl)-N-(2,2,6,6-tetramethyl-4-piperidyl)amino]propoxy}phenyl]propane, obtained as described in Example 17, and 1.44 g of sodium hydride in 150 ml of N,N-dimethylformamide was heated, with stirring, at 70°–80° C. for 2 hours. The reaction mixture was then cooled to ambient temperature and 10.3 g of benzyl bromide were added. The mixture was then heated, with stirring, at 100°–110° C. for 4 hours. At the end of this time, the solvent was removed from the reaction mixture by evaporation in vacuo, and the residue was dissolved in benzene and the benzene solution was washed, in turn, with a 5% w/w aqueous solution of sodium carbonate and with water. The washed solution was then dried over anhydrous potassium carbonate. The solvent was removed from the benzene solution by evaporation under reduced pressure and the residue thus obtained was purified by column chromatography through silica gel eluted with a 20:4:2:1 by volume mixture of ethyl acetate, benzene, ethanol and triethylamine. The desired compound was obtained in the form of an pale yellow, very viscous product having an $R_f$ value of 0.32 on thin layer chromatography on silica gel developed with a 20:4:2:1 by volume mixture of ethyl acetate, benzene, ethanol and triethylamine.

EXAMPLE 24

2,2-Bis[4-{2-acetoxy-3-[N-(2-acetoxyethyl)-N-(1-acetyl-2,2,6,6-tetramethyl-4-piperidyl)amino]propoxy}phenyl]propane (Compound No. 178)

A mixture of 200 ml of acetic anhydride and 7.4 g of 2,2-bis[4-{2-hydroxy-3-[N-(2-hydroxyethyl)-N-(2,2,6,6-tetramethyl-4-piperidyl)amino]propoxy}phenyl]propane, obtained as described in Example 17, was reacted in a manner similar to that described in Example 13, giving the desired compound in the form of a pale yellow, very viscous product. The compound had an $R_f$ value of 0.61 on thin layer chromatography on silica gel developed with a 20:4:2:1 by volume mixture of ethyl acetate, benzene, ethanol and triethylamine.

EXAMPLE 25

2,2-Bis[4-{2-benzoyloxy-3-[N-(2-benzoyloxyethyl)-N-(2,2,6,6-tetramethyl-4-piperidyl)amino]propoxy}phenyl]propane (Compound No. 181)

A mixture of 13.6 g of benzoic anhydride and 7.4 g of 2,2-bis[4-{2-hydroxy-3-[N-(2-hydroxyethyl)-N-(2,2,6,6-tetramethyl-4-piperidyl)amino]propoxy}phenyl]propane, obtained as described in Example 17, was heated, with stirring, at 110°–120° C. for 4 hours. At the end of this time, the reaction mixture was dissolved in 200 ml of benzene and the benzene solution was washed, in turn, with a 5% w/w aqueous solution of sodium carbonate and with water; the washed solution was then dried over anhydrous potassium carbonate. The solvent was then removed from the benzene solution by evaporation under reduced pressure and the resulting residue was purified by column chromatography through silica gel eluted with a 20:4:2:1 by volume mixture of ethyl acetate, benzene, ethanol and triethylamine. The desired compound was obtained in the form of a pale yellow, very viscous product having an $R_f$ value of 0.36 on thin layer chromatography on silica gel developed with a 20:4:2:1 by volume mixture of ethyl acetate, benzene, ethanol and triethylamine.

EXAMPLE 26

Stabilization of polypropylene

Mixtures were made from 100 parts of polypropylene powder (melt flow index about 18), 0.2 parts of stearyl 3-(4-hydroxy-3,5-di-t-butylphenyl)propionate (an antioxidant) and 0.25 part of each in turn of the stabilizers shown in following Table 1. The resulting mixtures were blended and homogenized by means of a Brabender Plastograph at 200° C. for 10 minutes. Each mixture thus obtained was pressed in a laboratory press to form a sheet 2–3 mm thick. Each sheet was compression-moulded in a hydraulic press at 260° C. for 6 minutes under a pressure of 12 tons and then immediately placed into cold water, forming a film of thickness 0.5 mm. The compression moulding procedure was then repeated, giving a film of thickness 0.1 mm. Control sheets were also made from identical compositions, except that they contained no stabilizer.

Each film was then cut into 50×120 mm test specimens, which were exposed to light in a Sunshine Weather Meter at a black panel temperature of 63±3° C. and examined periodically to determine the retention of elongation at break. The test results are reported in Table 1 as a ratio of the time required for the test specimens to reach 50% elongation at break when a stabilizer was used to the time required for a test specimen to reach 50% elongation at break when no stabilizer was used. In the Table, the compounds are identified by the numbers previously assigned to them. The results are also reported for a similar composition containing the known stabilizer Tinuvin 327, a Trade Mark for 2-(2-hydroxy-3,5-di-t-butylphenyl)-5-chlorobenzo-1,2,3-triazole, sold by Ciba-Geigy AG.

Table 1

| Stabilizer | ratio | Stabilizer | ratio |
|---|---|---|---|
| 4 | 4.7 | 98 | 5.3 |
| 5 | 4.9 | 149 | 5.4 |
| 16 | 4.3 | 172 | 4.4 |
| 17 | 6.4 | 227 | 5.6 |
| 21 | 5.7 | 232 | 4.8 |
| 22 | 5.0 | 237 | 5.5 |
| 70 | 4.6 | 239 | 7.9 |
| 71 | 4.8 | 252 | 6.2 |
| 73 | 4.6 | 255 | 5.1 |
| 90 | 3.1 | Tinuvin 327 | 2.0 |

EXAMPLE 27

Stabilization of ABS resin

Mixtures were made from 100 parts of acrylonitrile/butadiene/styrene (ABS) resin ("Kane-Ace B-12", trade name of Kanegafuchi Chemical Industries Co. Ltd.) and 0.5 part of each in turn of the stabilizers of the invention indicated in Table 2. The resulting mixtures were blended and homogenized on a two-roll mill at 165° C. for 4 minutes, giving sheets about 0.5 mm thick. Control sheets either containing no stabilizer or containing the known stabilizer Tinuvin P were also made. The sheets were compression-moulded at 190° C. for 1 minute to a thickness of 0.5 mm, after which dumbell test specimens were preared from them and subjected to ultraviolet irradiation in a Sunshine Carbon Arc Lamp Weather Meter for 50 hours. After irradiation, the retention of ultimate elongation and of ultimate tensile strength were measured by standard methods. The results are shown in Table 2.

Table 2

| Stabilizer | Retention of elongation (%) | Retention of tensile strength (%) |
|---|---|---|
| 4 | 63 | 75 |
| 17 | 60 | 72 |
| 71 | 61 | 74 |
| 90 | 64 | 75 |
| 149 | 62 | 73 |
| 227 | 62 | 74 |
| 239 | 61 | 75 |
| None | 19 | 67 |
| Tinuvin P | 43 | 67 |

EXAMPLE 28

Stabilization of polyurethane

Mixtures were made from 100 parts of an aromatic polyester-type polyurethane ("Estane 5707", Trade Mark of Goodrich Co.) and 0.5 part of each in turn of the stabilizers of the invention indicated in Table 3; the mixtures were then each dissolved in 400 parts of dimethylformamide. The resulting solutions were used to cast films about 500μ thick on a plain glass plate. After air-drying, each film was further dried at 60° C. for 10 minutes and at 140° C. for 6 minutes, giving a film about 100μ thick. The films thus formed were exposed to ultaviolet radiation in a Sunshine Carbon Arc Lamp Weather Meter for 200 hours and the degree of yellowing was measured. The procedure was repeated with control sheets either containing no stabilizer or containing the known stabilizer Tinuvin P. The results are shown in Table 3.

Table 3

| Stabilizer | Yellowness index before irradiation | Yellowness index after irradiation |
|---|---|---|
| 4 | 2.1 | 22.7 |
| 17 | 1.9 | 21.6 |
| 71 | 1.9 | 24.1 |
| 90 | 1.8 | 22.3 |
| 149 | 2.0 | 21.8 |
| 227 | 1.9 | 20.2 |
| 239 | 2.1 | 23.9 |
| None | 2.0 | 49.7 |
| Tinuvin P | 1.9 | 36.8 |

We claim:
1. A compound of formula (I):

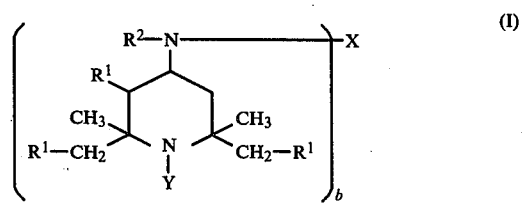

wherein
$R^1$ represents a hydrogen atom or a methyl group;
$R^2$ represents a hydrogen atom, an alkyl group having from 1 to 18 carbon atoms, a cycloalkyl group having from 5 to 7 carbon atoms, an unsubstituted phenyl group, a phenyl group having one or more substituents selected from $C_1$–$C_4$ alkyl and $C_1$–$C_4$ alkoxy groups, a naphthyl group, an aralkyl group having 7 or 8 carbon atoms, an aliphatic, aromatic, araliphatic or alicyclic acyl group having up to 18 carbon atoms wherein the aryl moiety is unsubstituted or has one or more substituents selected from $C_1$–$C_4$ alkyl and hydroxy groups, an alkylsulphonyl group having from 1 to 4 carbon atoms, a phenylsulphonyl group which is unsubstituted or has one or more $C_1$–$C_{12}$ alkyl substituents, a group of formula —CONHR$^3$ wherein R$^3$ represents an alkyl group having from 1 to 18 carbon atoms, an unsubstituted phenyl group, a substituted phenyl group having one or more substituents selected from methyl groups, chlorine atoms and bromine atoms, a naphthyl group or a cycloalkyl group having from 5 to 7 carbon atoms, or a group of formula —CH$_2$CH$_2$OZ;

when R$^2$ represents a hydrogen atom, Z of X and Y as defined herein below represents a hydrogen atom and when R$^2$ represents a group other than a hydrogen atom, Z represents a hydrogen atom, an alkyl group having from 1 to 18 carbon atoms, an allyl group, a benzyl group, an aliphatic, aromatic, araliphatic or alicyclic acyl group having up to 18 carbon atoms wherein the aryl moiety is unsubstituted or has one or more substituents selected from $C_1$–$C_4$ alkyl and hydroxy groups, or a group of formula —CONHR$^9$ wherein R$^9$ represents an alkyl group having from 1 to 18 carbon atoms, an unsubstituted phenyl group, a phenyl group having one or more substituents selected from methyl groups, chlorine atoms and bromine atoms, a naphthyl or a cycloalkyl group having from 5 to 7 carbon atoms;

when R$^2$ represents a hydrogen atom, Y represents a hydrogen atom, an alkyl group having from 1 to 18 carbon atoms, an alkenyl group having 3 or 4 carbon atoms or a benzyl group, and, when R$^2$ represents a group other than a hydrogen atom, Y represents a hydrogen atom, an alkyl group having from 1 to 18 carbon atoms, an alkenyl group having 3 or 4 carbon atoms, a benzyl group, a 2,3-epoxypropyl group, an aliphatic acyl group having up to 18 carbon atoms or one of the groups of formulae

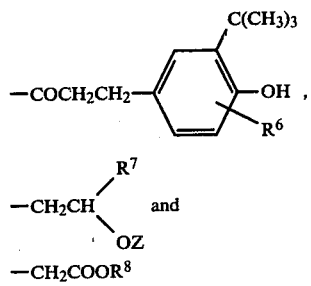

wherein
R$^6$ represents an alkyl group having from 1 to 4 carbon atoms;
R$^7$ represents a hydrogen atom, a methyl group or a phenyl group;
R$^8$ represents an alkyl group having from 1 to 18 carbon atoms; and
Z is as defined above;
b represents 2 or 3; and
when b=2, X represents one of the groups of formulae

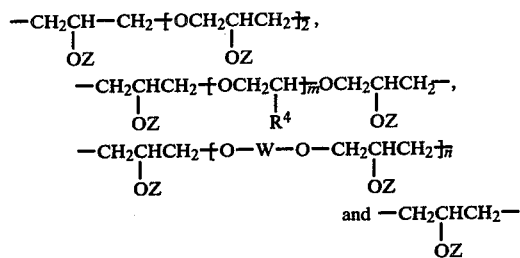

m represents an integer of from 1 to 10;
n represents an integer of from 1 to 10;
R$^4$ represents a hydrogen atom or a methyl group;
W represents one of the groups of formulae

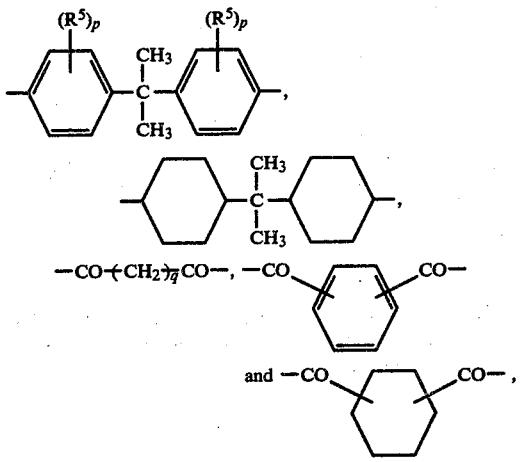

wherein
p represents 0, 1 or 2;
R$^5$ represents a halogen atom;
q represents an integer of from 1 to 10; and
Z is as defined above;
when b=3, X represents one of the groups of formulae

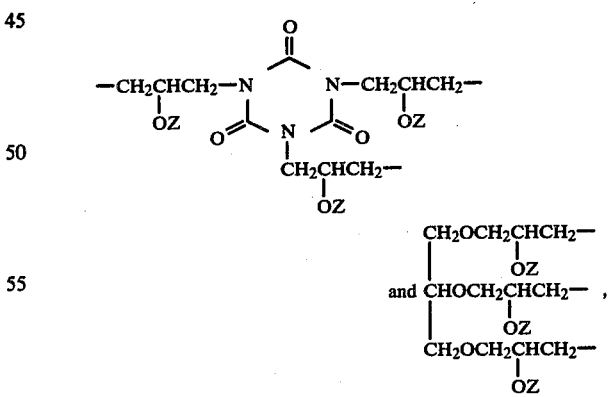

wherein Z is as defined above,
and an acid addition salt thereof.

2. A compound as claimed in claim 1, wherein R$^1$ represents a hydrogen atom.

3. A compound as claimed in claim 1, wherein R$^2$ represents a hydrogen atom, an alkyl group having from 1 to 8 carbon atoms, a cyclohexyl group, an alkanoyl group having from 2 to 12 carbon atoms, a benzoyl group or a group of formula —CH₂CH₂OZ' wherein Z' represents a hydrogen atom, an acetyl group or a benzoyl group.

4. A compound as claimed in claim 1, wherein X represents a group of formula

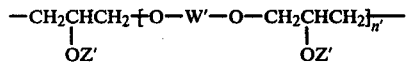

wherein W' represents one of the groups of formulae

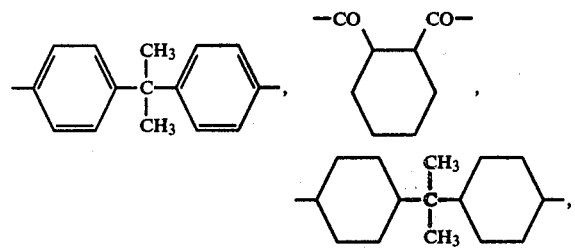

—CO[CH₂]$_q$CO— and —CH₂CH₂— wherein
q is an integer of from 1 to 10;
Z' represents a hydrogen atom, an acetyl group or a benzoyl group, and n' is 0 or 1.

5. A compound as claimed in claim 4, wherein W' represents one of the groups of formulae

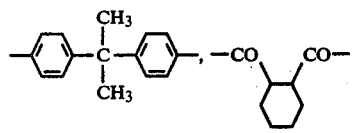

n' represents 1.

6. A compound as claimed in claim 1, wherein Y represents a hydrogen atom, a methyl group, an allyl group or an acetyl group.

7. A compound as claimed in claim 1, wherein Z represents a hydrogen atom, an acetyl group or a benzoyl group.

8. A compound of formula (II):

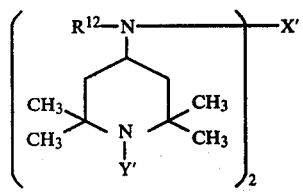

wherein
R¹² represents a hydrogen atom, an alkyl group having from 1 to 8 carbon atoms or a 2-hydroxyethyl group;
X' represents a group of formula

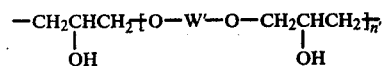

wherein
W' represents one of the groups of formulae

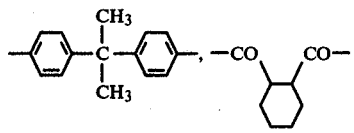

and —CH₂CH₂—, and
n' represents 0 or 1; and
Y' represents a hydrogen atom or a methyl group.

9. A polymeric composition stabilized against photo- and thermal deterioration comprising a synthetic polymer and a stabilizing amount of stabilizer selected from the group consisting of compounds of formula (I):

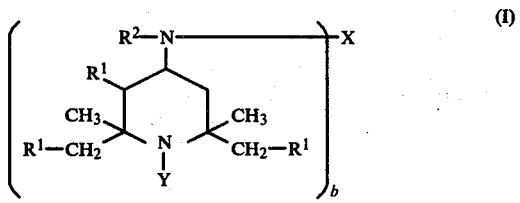

wherein
R¹ represents a hydrogen atom or a methyl group;
R² represents a hydrogen atom, an alkyl group having from 1 to 18 carbon atoms, a cycloalkyl group having from 5 to 7 carbon atoms, an unsubstituted phenyl group, a phenyl group having one or more substituents selected from C₁-C₄ alkyl and C₁-C₄ alkoxy groups, a naphthyl group, an aralkyl group having 7 or 8 carbon atoms, an aliphatic, aromatic, araliphatic or alicyclic acyl group having up to 18 carbon atoms wherein the aryl moiety is unsubstituted or has one or more substituents selected from C₁-C₄ alkyl and hydroxy groups, an alkylsulphonyl group having from 1 to 4 carbon atoms, a phenylsulphonyl group which is unsubstituted or has one or more C₁-C₁₂ alkyl substituents, a group of formula —CONHR³ wherein
R³ represents an alkyl group having from 1 to 18 carbon atoms, an unsubstituted phenyl group, a substituted phenyl group having one or more substituents selected from methyl groups, chlorine atoms and bromine atoms, a naphthyl group or a cycloalkyl group having from 5 to 7 carbon atoms, or a group of formula —CH₂CH₂OZ;
when R² represents a hydrogen atom, Z of X and Y as defined herein below represents a hydrogen atom and when R² represents a group other than a hydrogen atom, Z represents a hydrogen atom, an alkyl group having from 1 to 18 carbon atoms, an allyl group, a benzyl group, an aliphatic, aromatic, araliphatic or alicyclic acyl group having up to 18 carbon atoms wherein the aryl moiety is unsubstituted or has one or more substituents selected from C₁-C₄ alkyl and hydroxy groups, or a group of formula —CONHR⁹ wherein
R⁹ represents an alkyl group having from 1 to 18 carbon atoms, an unsubstituted phenyl group, a phenyl group having one or more substituents selected from methyl groups, chlorine atoms and bromine atoms, a naphthyl or a cycloalkyl group having from 5 to 7 carbon atoms;
when R² represents a hydrogen atom, Y represents a hydrogen atom, an alkyl group having from 1 to 18 carbon atoms, an alkenyl group having 3 or 4 carbon atoms or a benzyl group, and, when R² represents a group other than a hydrogen atom, Y represents a hydrogen atom, an alkyl group having from 1 to 18 carbon atoms, an alkenyl group having 3 or 4 carbon atoms, a benzyl group, a 2,3-epoxypropyl group, an aliphatic acyl group having up to 18 carbon atoms or one of the groups of formulae

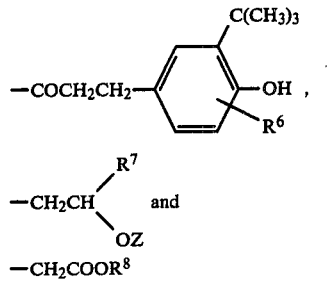

wherein
$R^6$ represents an alkyl group having from 1 to 4 carbon atoms;
$R^7$ represents a hydrogen atom, a methyl group or a phenyl group;
$R^8$ represents an alkyl group having from 1 to 18 carbon atoms; and
Z is as defined above;
b represents 2 or 3; and
when b=2, X represents one of the groups of formulae

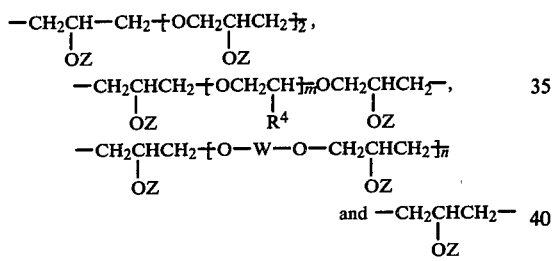

m represents an integer of from 1 to 10;
n represents an integer of from 1 to 10;
$R^4$ represents a hydrogen atom or a methyl group;
W represents one of the groups of formulae

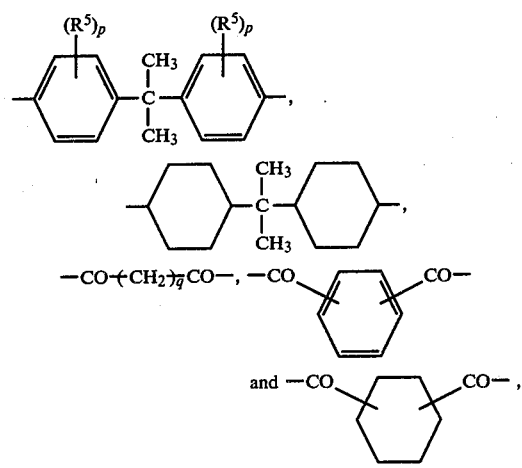

wherein
p represents 0, 1 or 2;

$R^5$ represents a halogen atom;
q represents an integer of from 1 to 10; and
Z is as defined above;
when b=3; X represents one of the groups of formulae

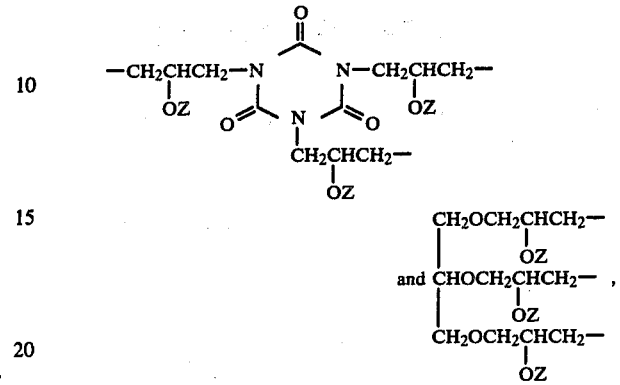

wherein Z is as defined above,
and acid addition salts thereof.

10. A composition as claimed in claim 9, wherein $R^1$ represents a hydrogen atom.

11. A composition as claimed in claim 9, wherein $R^2$ represents a hydrogen atom, an alkyl group having from 1 to 8 carbon atoms, a cyclohexyl group, an alkanoyl group having from 2 to 12 carbon atoms, a benzoyl group or a group of formula —CH$_2$CH$_2$OZ' wherein Z' represents a hydrogen atom, an acetyl group or a benzoyl group.

12. A composition as claimed in claim 9, wherein X represents a group of formula

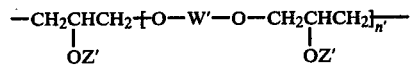

wherein
W' represents one of the groups of formulae

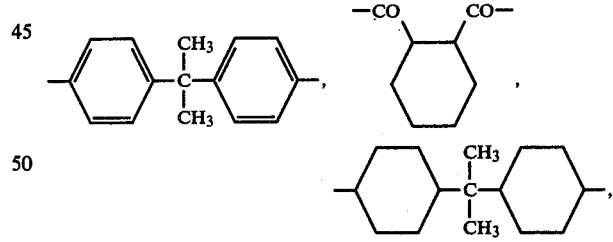

—CO[CH$_2$]$_q$CO— and —CH$_2$CH$_2$— wherein
q is an integer of from 1 to 10;
Z' represents a hydrogen atom, an acetyl group or a benzoyl group, and n' is 0 or 1.

13. A composition as claimed in claim 12, wherein W' represents one of the groups of formulae

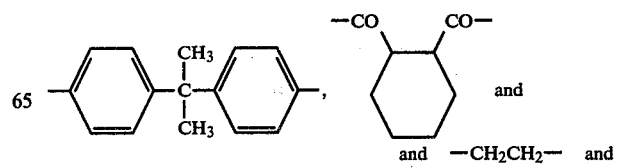

n' represents 1.

14. A composition as claimed in claim 9, wherein Y represents a hydrogen atom, a methyl group, an allyl group or an acetyl group.

15. A composition as claimed in claim 9, wherein Z represents a hydrogen atom, an acetyl group or a benzoyl group.

16. A composition as claimed in claim 9, wherein said stabilizer is selected from compounds of formula (II):

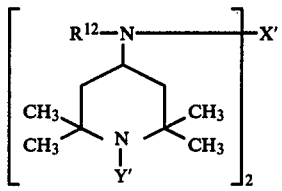

(II)

wherein $R^{12}$ represents a hydrogen atom, an alkyl group having from 1 to 8 carbon atoms or a 2-hydroxyethyl group;

X' represents a group of formula

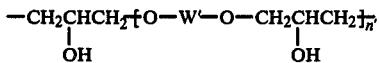

wherein

W' represents one of the groups of formulae

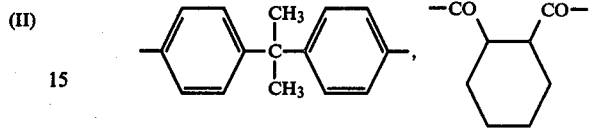

and —CH$_2$CH$_2$—, and n' represents 0 or 1; and

Y' represents a hydrogen atom or a methyl group.

* * * * *